(12) United States Patent
Ragauskas et al.

(10) Patent No.: US 7,938,780 B2
(45) Date of Patent: May 10, 2011

(54) ULTRASONIC METHOD AND APPARATUS FOR MEASURING INTRACRANIAL CONTENTS VOLUME CHANGE

(75) Inventors: Arminas Ragauskas, Kaunas (LT); Gediminas Daubaris, Kaunas (LT); Vytautas Petkus, Kaunas (LT); Renaldas Raisutis, Kaunas (LT)

(73) Assignee: UAB Vittamed Technologijos (LT)

( * ) Notice: Subject to any disclaimer, the term of this patent is extended or adjusted under 35 U.S.C. 154(b) by 652 days.

(21) Appl. No.: 12/023,325

(22) Filed: Jan. 31, 2008

(65) Prior Publication Data

US 2009/0198137 A1    Aug. 6, 2009

(51) Int. Cl.
A61B 8/00 (2006.01)
A61B 8/14 (2006.01)

(52) U.S. Cl. ......... 600/449; 600/438; 600/448; 600/459

(58) Field of Classification Search ................ 600/438, 600/442, 447, 449, 437, 459, 448
See application file for complete search history.

(56) References Cited

U.S. PATENT DOCUMENTS

| | | | |
|---|---|---|---|
| 3,872,858 A | 3/1975 | Hudson et al. | 128/2 |
| 4,043,321 A | 8/1977 | Soldner et al. | 128/2 |
| 4,062,354 A | 12/1977 | Taylor et al. | 128/2 |
| 4,312,361 A | 1/1982 | Nicholson et al. | 128/748 |
| 4,690,149 A | 9/1987 | Ko | 128/635 |
| 4,819,648 A | 4/1989 | Ko | 128/635 |
| 4,971,061 A | 11/1990 | Kageyama et al. | 128/660.02 |
| 4,984,567 A | 1/1991 | Kageyama et al. | 128/660.02 |
| 5,074,310 A | 12/1991 | Mick | 128/748 |
| 5,117,835 A | 6/1992 | Mick | 128/748 |
| 5,388,583 A | 2/1995 | Ragauskas et al. | 128/661.05 |
| 5,411,028 A | 5/1995 | Bonnefous | 128/661.08 |
| 5,617,873 A | 4/1997 | Yost et al. | 128/748 |
| 5,919,144 A | 7/1999 | Bridger et al. | 600/561 |
| 5,993,398 A | 11/1999 | Alperin | 600/561 |
| 6,117,089 A | 9/2000 | Sinha | 600/561 |
| 6,245,016 B1 | 6/2001 | Daft et al. | 600/443 |
| 6,387,051 B1 * | 5/2002 | Ragauskas et al. | 600/438 |
| 6,702,743 B2 | 3/2004 | Michaeli | 600/438 |
| 6,875,176 B2 | 4/2005 | Mourad et al. | 600/442 |
| 7,175,599 B2 * | 2/2007 | Hynynen et al. | 600/443 |
| 7,300,414 B1 * | 11/2007 | Holland et al. | 604/22 |

* cited by examiner

*Primary Examiner* — Long V Le
*Assistant Examiner* — Katherine L Fernandez
(74) *Attorney, Agent, or Firm* — St. Onge Steward Johnston & Reens LLC

(57) ABSTRACT

An ultrasonic method for indicating a characteristic of intracranial components' volume changes includes the transmission of broadband ultrasound from a transmitting transducer positioned on one side of a human head to a receiving transducer located on another side of the human head with decomposition of the received signal into narrowband components and determination therefrom of group delay, phase angle and attenuation as a basis for derivation of the characteristic of the intracranial media.

33 Claims, 25 Drawing Sheets

LEGEND

ULTRASONIC METHOD AND APPARATUS FOR MEASURING INTRACRANIAL CONTENTS VOLUME CHANGE

FIELD OF THE INVENTION

The present invention relates to the measurement and monitoring of intracranial pressure changes caused by intracranial contents' volume changes. More particularly it relates to an apparatus and method for non-invasive measurement of the brain parenchyma blood volume and brain tissue volume using transmission of ultrasonic pulses through the human head.

BACKGROUND OF THE INVENTION

The measurement of intracranial pressure (ICP) is important in diagnosing and treating various pathophysiological conditions caused by head trauma, hemorrhage, tumors, inflammatory diseases and the like. Several techniques have been used to measure ICP. Conventional invasive ICP measurement techniques require surgical passage through the skull bone into the brain ventricles, parenchyma, or the region between the skull and dura matter to implant a measuring transducer.

A non-invasive ICP measurement technique has been suggested that determines displacements of the tympanic membrane of the ear. However, it has not been possible to obtain a good correlation with ICP because determination of ICP by this method is complicated by the compressible air space between the pressure source and the interrogation point.

Another non-invasive ICP measurement method measures the electromagnetic impedance response of the brain to induced fields, and correlates the response to ICP. Such techniques are disclosed in U.S. Pat. Nos. 4,690,149 and 4,819,648 to Ko.

Another non-invasive ICP measurement technique that has been attempted involves ultrasonic imaging to detect relative displacements of tissue boundaries within the brain. The displacements may be associated with fluid build-up and compression or dilation of brain vessels, which permits determination of ICP through an independent calibration of compressibility. An alternate non-invasive ultrasonic technique involves the measurement of blood flow in the carotid artery by ultrasonic excitation of the artery and determination of Doppler frequency shift.

Various types of ultrasonic ICP measurement techniques are disclosed in France Patent FR, A, 2318420 to Guiset, U.S. Pat. No. 3,872,858 to Hudson et al., U.S. Pat. No. 4,043,321 to Soldner et al., U.S. Pat. No. 4,971,061 to Kageyama et al., U.S. Pat. No. 4,984,567 to Kageyama et al., U.S. Pat. No. 5,388,583 to Ragauskas et al., U.S. Pat. No. 5,411,028 to Bonnefous, U.S. Pat. No. 5,617,873 to Yost et al. and U.S. Pat. No. 5,919,144 to Bridger et al. Such techniques involve the transmission of ultrasonic waves typically having frequencies on the order 0.1 MHz . . . 0.5 MHz or 1.0 MHz . . . 5.0 MHz into the intracranial media.

Each of the patents cited above is incorporated herein by reference.

Despite the above-noted attempts to develop non-invasive ICP measurement technique, a need still exists for a non-invasive ICP measurement apparatus and method which can accurately measure ICP absolute value and all possible ICP waves without skull penetration and which poses no health risks during long-term monitoring. On the other hand, ICP changes are caused by intracranial media components' volume changes. These components are arterial and venous blood, cerebrospinal fluid (CSF), brain tissues and intersticial fluid. For the targeted therapy of raised ICP, it is necessary to know which intracranial component has increased in volume. However, using known ultrasonic ICP measuring methods and apparatus, it is still impossible to identify which intracranial component is the cause of ICP increment. Therefore, a need exists for a method and apparatus for simultaneous measurement and monitoring intracranial blood volume, CSF volume, and brain parenchyma tissue volume. The only known method and apparatus for the measurement of blood volume inside the brain parenchymal acoustic path know to the inventors is U.S. Patent No. 5,388,583.

However, known ultrasonic non-invasive ICP measuring apparatus and methods have the many limitations. For example, the known methods and apparatus:

are affected by the head external tissues blood flow phenomena;
 are uncomfortable due to direct contact of the rigid surface of the ultrasonic transducers with the patient's extracranial tissues;
 can eliminate extracranial tissue volume pulsation with only limited accuracy due to a limited signal-to-noise ratio in the ultrasonic echo from the surface of skull measurement channels;
 can require the device operator to manually perform interactive ultrasonic signal adjustment procedures that are too lengthy and too sophisticated for emergency room or intensive care unit situations; and
 make it impossible to define the intracraniospinal compliance changes using known ultrasonic non-invasive methods and devices.

SUMMARY OF THE INVENTION

Accordingly, one objective of the invention is to substantially eliminate the influence of external tissue pulsation on the non-invasively measured data about the shape of intracranial volumetric pulse waves.

Another object is to increase the signal-to-noise ratio of the ultrasonic echo signal by using time division multiplexing of the transintracranial transmitted ultrasonic signals and by transmitting the ultrasonic signals in the direction that produce the highest echo signal-to-noise ratio.

Still another object is to scan the ultrasonic signal transmission and receiving directions in order to identify the optimal transintracranial and echo signal directions.

Yet another object is to switch the ultrasonic transducer effective diameter in order to get two optimal near field zone dimensions for transintracranial and echo signal transmission by using the proposed new disc and ring type ultrasonic transducer.

Another object is switching of ultrasonic cMUT (capacitative micromachined ultrasound transducer) type two-dimensional transducers transmission/receiving directions and also adaptive focusing of cMUT on the skull surface when the transmission direction is the same as the echo signal direction.

Still another object is to eliminate possible discomfort for a patient due to the direct contact of extracranial tissues with the rigid surface of the ultrasonic transducer by applying an ultrasound gel pad between the extracranial tissue and the active surface of the ultrasonic transducer.

Yet another object is the fast and real-time adjustment of ultrasonic signal amplitudes, selection of ultrasonic signal positions in time, and identification of informative signal zero crossing points in order to eliminate operator errors and in order to save time of non-invasive device preparatory procedures before the non-invasive measurement.

Another object to non-invasively determine intracraniospinal compliance changes using the proposed new non-invasive compliance estimation index.

These and other objects are achieved by the provision of a device for measuring intracranial contents' volume changes which cause pressure changes of a patient head.

In one embodiment, a device for measuring intracranial contents' volume changes which cause pressure changes of a patient's head is provided comprising a first gel pad and a second gel pad positioned on either side of the patient's head respectively and a first ultrasonic transducer and a second ultrasonic transducer positioned adjacent to the first and second gel pads respectively. The device further comprises a first two-dimensional scanner positioned adjacent to the first ultrasonic transducer and a second two-dimensional scanner positioned adjacent to the second ultrasonic transducer. The device is provided such that the first and second ultrasonic transducers each have a piezoceramic disc and a piezoceramic ring encircling the piezoceramic disc.

In another embodiment a device for measuring intracranial content volume changes which cause pressure changes of a patient's head is provided comprising a first gel pad positioned on a first side of the patient's head and a second gel pad positioned on a second side of the patient's head. The device further comprises a first ultrasonic transducer positioned adjacent to the first gel pad, the first ultrasonic transducer including a first piezoceramic disc and a first piezoceramic ring encircling the first piezoceramic disc. The device still further includes a second ultrasonic transducer positioned adjacent to the second gel pad, the second ultrasonic transducer including a second piezoceramic disc and a second piezoceramic ring encircling the second piezoceramic disc. The device also includes a first scanner positioned adjacent to the first ultrasonic transducer and a second scanner positioned adjacent to the second ultrasonic transducer. Finally, the device also comprises a time division multiplexer coupled to the first and second ultrasonic transducers, a computer coupled to the time division multiplexer and a display coupled to the computer.

In still another embodiment a method for measuring intracranial content volume changes which cause pressure changes of a patient's head is provided comprising the steps of positioning a first gel pad on a first side of the patient's head, positioning a second gel pad on a second side of the patient's head and positioning a first ultrasonic transducer adjacent to the first gel pad, the first ultrasonic transducer having a first piezoceramic disc and a first piezoceramic ring encircling the first piezoceramic disc. The method further comprises the steps of positioning a second ultrasonic transducer adjacent to the second gel pad, the second ultrasonic transducer having a second piezoceramic disc and a second piezoceramic ring encircling the second piezoceramic disc, positioning a first scanner adjacent to the first ultrasonic transducer and positioning a second scanner adjacent to the second ultrasonic transducer. The method still further comprises the steps of generating first and second ultrasonic pulses with the first and second ultrasonic transducers respectively, transmitting the ultrasonic pulses through the patient's head and receiving the ultrasonic pulses with the first and second scanners.

In yet another embodiment a method for measuring intracranial content volume changes which cause pressure changes of a patient's head is provided comprising the steps of generating a first ultrasonic pulse with a first ultrasonic transducer and transmitting the first ultrasonic pulse through a patients head. The method further comprises the steps of generating a second ultrasonic pulse with a second ultrasonic transducer, the second ultrasonic transducer positioned on a substantially opposite side of the patient's head from the first ultrasonic transducer and transmitting the second ultrasonic pulse through a patients head. The method also comprises the steps of generating a first electrical pulse corresponding to the transmitted first ultrasonic pulse, measuring a first echo pulse corresponding to an echo signal of the transmitted first ultrasonic pulse and generating a first echo electrical pulse corresponding to the measured first echo pulse. The method still further comprises the steps of generating a second electrical pulse corresponding to the transmitted second ultrasonic pulse, measuring a second echo pulse corresponding to an echo signal of the transmitted second ultrasonic pulse and generating a second echo electrical pulse corresponding to the measured second echo pulse.

Other objects of the invention and its particular features and advantages will become more apparent from consideration of the following drawings and accompanying detailed description.

DETAILED DESCRIPTION OF THE INVENTION

Figure 1:
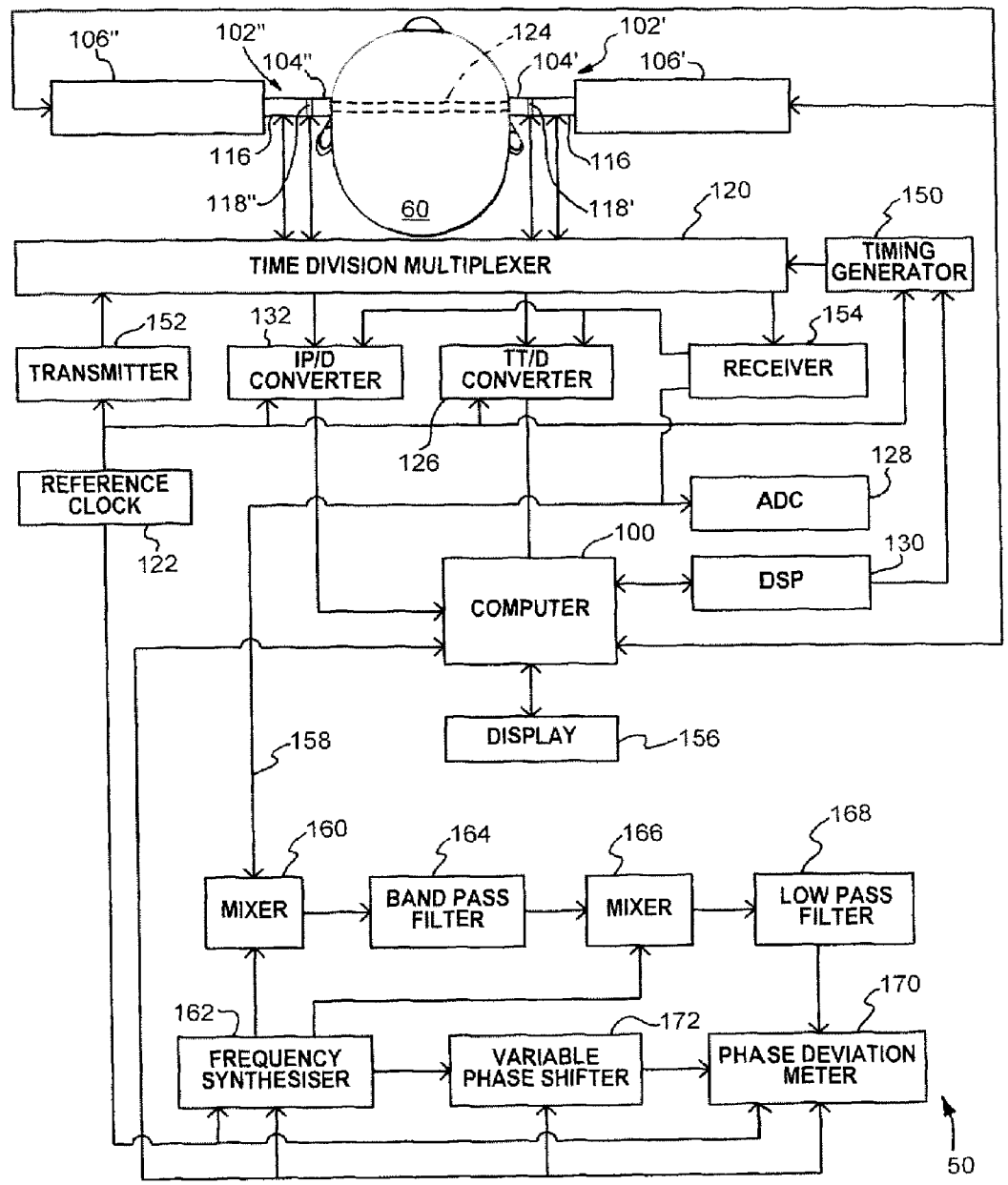
FIG. 1 is a block diagram of one embodiment of the present invention.

The following hypotheses were postulated:

a) Variations of acoustic properties of the human brain such as ultrasound attenuation and ultrasound velocity are associated with blood, cerebrospinal fluid or brain tissue volume changes.

b) These variations of acoustic properties of the human brain can be detected non-invasively and in real time.

What was developed is a non-invasive technology for measuring the ultrasound velocity relative changes and ultrasound attenuation inside the parenchymal acoustic path crossing the human brain to confirm this hypothesis.

In one embodiment, the method is based on the transmission of short ultrasonic pulses with a central spectral frequency of 2.0 MHz from one side of the head and the receiving on the other side the ultrasonic pulses which were propagated through the external tissues, skull and intracranial media. What is detected is the ultrasound time-of-flight variations and ultrasound attenuation variations caused by the volume changes of intracranial media (cerebrospinal fluid, brain parenchyma tissue, arterial and venous blood) inside the parenchymal acoustic path. The acoustic properties of external tissues and skull are also measured separately by using echo method and the same ultrasonic signals as used for transmission through the human head. The effect of the external tissues and skull can therefore be eliminated from the subsequent ICP and intracranial components' volume (ICV) changes calculations.

The acoustic properties of the cerebrospinal fluid (CSF), brain tissues, skull and blood have different acoustic properties. Their respective values have been experimentally determined and are listed in Table 1 below.

TABLE 1

Attenuation parameters and sound speed of the media, used for cranial simulation.

| Media | Attenuation parameters | | Sound speed c (m/s) Under (1.8 MHz, 37° C.) | References |
|---|---|---|---|---|
| | $\alpha_o$, dB/(cm MHz$^\gamma$) | $\gamma$ | | |
| Skull bone | 11.089 | 1.89 | 2652 | [1, 2] |
| Blood | 0.212 | 1.27 | 1590 | [1, 2] |
| Brain tissue | 0.869 | 1.07 | 1563 | [1, 2] |
| CSF | 0.0023 | 1.99 | 1530 | [1, 2, 3] |

What was found was that if the distance $L_0$ between two hybrid ultrasonic transducers is fixed by a mechanical frame and equal to a constant, it is possible to detect the ultrasonic signals time-of-flight changes inside the acoustic path. The acoustic path can cross different structures of the human head. In this case, the ultrasound velocity relative changes caused by the volume changes of different intracranial compartments (cerebroventricles, blood vessels, cerebrospinal fluid compartments, parenchyma tissue volume) are equal to the measured time-of-flight relative changes.

A mathematical model was created for simulating the propagation of ultrasonic signal through the layered attenuating medium (human head) and dynamic physiological phenomena that cause changes of ICV and ICP.

If a broadband ultrasonic signal is propagated through a dispersive medium, it is attenuated, delayed, and the central frequency of the waveform is shifted down depending on media attenuation characteristics. Frequency dependent attenuation of biological tissues can be expressed by the power law function [1,4,5,6]:

$$\alpha(\omega) = \alpha_0 \omega^\gamma, \quad \text{Formula 1}$$

where $\alpha_0$ and $\gamma$ are the tissue-dependent attenuation parameters. For many biological tissues an anomalous dispersion phenomenon is observed ($1 \leq \gamma < 2$), i.e., higher frequency components of the ultrasound pulse spectrum travel at higher phase speeds than lower frequency components. This phenomenon causes the modulation of the central frequency.

The output signal g(t) is the convolution of the input signal r(t) and the impulse response of the media h(t) [4,7,8]:

$$g(t) = r(t) \oplus h(t). \quad \text{Formula 2}$$

The impulse response is calculated by taking the inverse Fourier transform of the frequency response of the media:

$$h(t) = FT^{-1}[H(\omega)] = FT^{-1}[A(\omega)e^{-j\Theta(\omega)x}] = FT^{-1}[e^{-\alpha(\omega)x}e^{j x \omega : V_p(\omega)}], \quad \text{Formula 3}$$

where $H(\omega)$ is the frequency response of the media, $A(\omega)$ is the magnitude function, $\Theta(\omega)$ is the phase angle per units distance, x is the distance of the ultrasound propagation, $V_p(\omega)$ is the phase velocity.

For simulating dispersion, attenuation and time delay of an ultrasonic signal, a spectrum decomposition method is used [4,9]. Using this method, a broadband ultrasonic signal is decomposed into narrowband components, and for each component a group delay, phase angle and attenuation parameter are calculated separately. To obtain the minimum reconstruction error, the Gaussian filters were chosen for decomposition [4]:

$$B_i(f) = \frac{1}{\pi} e^{-\left(\frac{f - f_L - (i-1)B}{B}\right)^2}, \quad i = 1, 2, \ldots, n \quad \text{Formula 4}$$

where $f_L = 0.6$ MHz is the center frequency of the lowest frequency filter, $f_H = 3.6$ MHz is the center frequency of the highest frequency filter, $B = (f_H - f_L)/(n-1)$ is the filter bandwidth constant for all filters (B=0.3 MHz), and n is the number of filters. The bandwidth of the filters B was chosen narrow enough so that the downshift of the signal center frequency in the i-th branch would be negligible [4].

For each decomposed narrowband component attenuation $\alpha_i$ is calculated according to the Formula 1, meanwhile the signal angular phase $\Theta_i$ and group delay $t_{gi}$ are defined as:

a) when $\gamma = 1$, a "nearly local model" developed by O'Donnel [10] is used. The signal angular phase and the group delay are:

$$\varphi_i = \frac{2\omega_i \alpha_0 x}{\pi}, \quad \text{Formula 5}$$

$$t_g = \frac{x}{V_g(\omega_i)} = \frac{x}{V_p(\omega_0)} - \frac{2\alpha_0 x}{\pi}\left(\ln\frac{\omega_i}{\omega_0} + 1\right), \quad \text{Formula 6}$$

b) when $1 < y \leq 2$, a "time.causal mode" proposed by Szabo [5] is used:

$$\varphi_i = -(y-1)\omega_i^y \alpha_0 x \tan\left(\frac{y\pi}{2}\right), \quad \text{Formula 7}$$

$$t_g = \frac{x}{V_g(\omega_i)} \quad \text{Formula 8}$$

$$= \frac{x}{V_p(\omega_0)} - \alpha_0 x \tan\left(\frac{y\pi}{2}\right)(y\omega_i^{y-1} - \omega_0^{y-1}).$$

While developing a mathematical model of a human cranium it was assumed that the total head volume is 1600 ml that consists of 80% brain tissue, 10% cerebrospinal flow (CSF), and 10% blood. The assumption was made that the ultrasonic signal propagates through the cranium 15 cm on a straight line and the thickness of cranial components according to the proportions presented above are 12 cm of brain tissue, 1.5 cm of CSF and 1.5 cm of blood, respectively. Also the thickness of a cranium bone is included and the total distance of signal propagation in the bone and in the external tissues is 1.6 cm.

Our computer modeling of ultrasound pulse propagation through the human head in which dynamic physiological phenomena (vasodilatation and vasoconstriction) occur shows that there are two ways of getting information about the changes of craniospinal volume or ICP. The change of ICP is related to the deviation of a craniospinal volume. Simulated physiological phenomena show, that in vasodilatation cases, an increase in the brain blood volume inside the acoustic path within the physiological limits causes a decrease in the received ultrasonic signal's first period and the signal propagation time. An increase in brain tissue volume and a decrease in CSF volume inside the acoustic path causes an increase in the ultrasonic signal's first period and the decrease of the signal's time-of-flight. The dependence of both the deviation of the signal time-of-flight and the deviation of the first period on the craniospinal volume deviation is linear (with the error less than +/−1%) in the investigated pathophysiological range of craniospinal volume changes from 0 ml to 20.0 ml and ICP changes from 10.0 mmHg until 80.0 mmHg. Modeling also shows that the pathophysiological variations of the cerebral blood or parenchyma tissue volume inside the acoustic path and ICP are detectable if our non-invasive technique is used. Modeling also shows that it is possible to eliminate the acoustic properties of external tissues, skull, and dura matter and also eliminate the possible Doppler shift in real-time by applying the echo method, the fast commutation (500 Hz) of signal transmission direction, and the same ultrasonic signals. In this case special ultrasonic transducers for such purposes need to be created and the digital signal processing technology of ultrasonic signals need to be introduced into our monitors.

As shown in FIG. 1, an embodiment of the apparatus 50 includes a computer 100 and connected display 156, electronic block, two ultrasonic transmitting/receiving transducers 102', 102", two two-dimentional (2D) scanners 106', 106" of the transmission and receiving direction of ultrasonic transducers, two ultrasound gel pads 104', 104" and a mechanical frame 108 (not shown) for fixation of the ultrasonic transducers on a patient's head 60.

Figure 2:
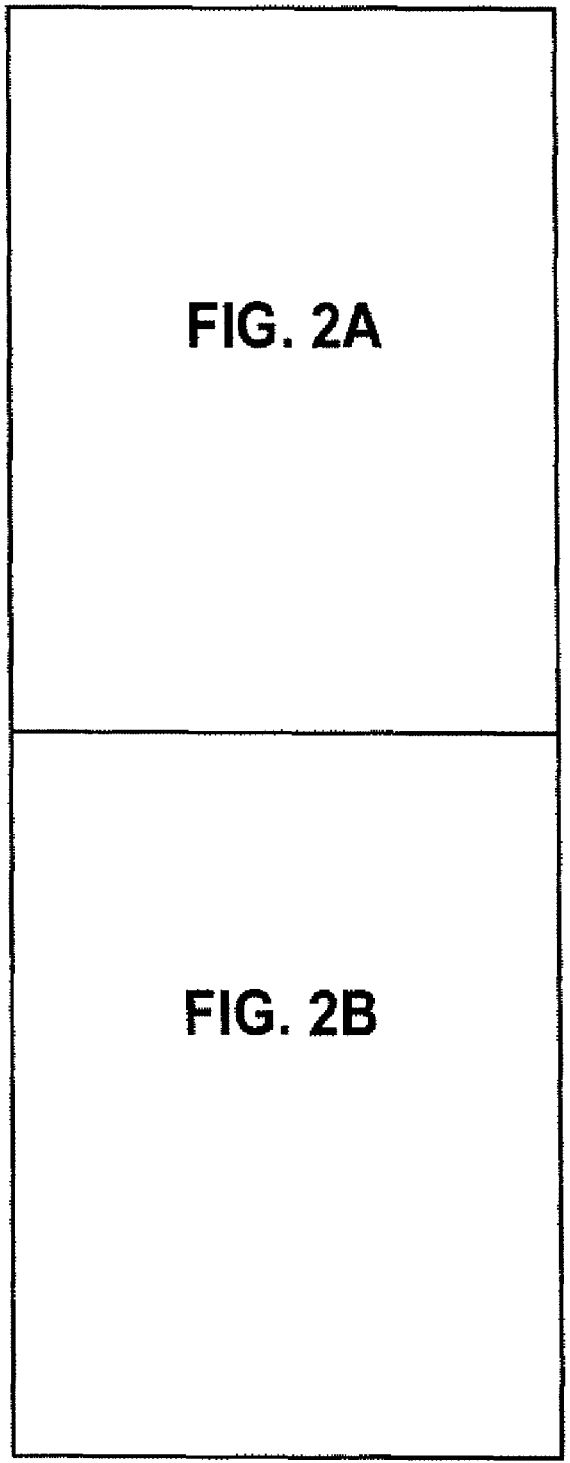
FIG. 2 is a flow chart of the embodiment according to FIG. 1.
Figure 2:
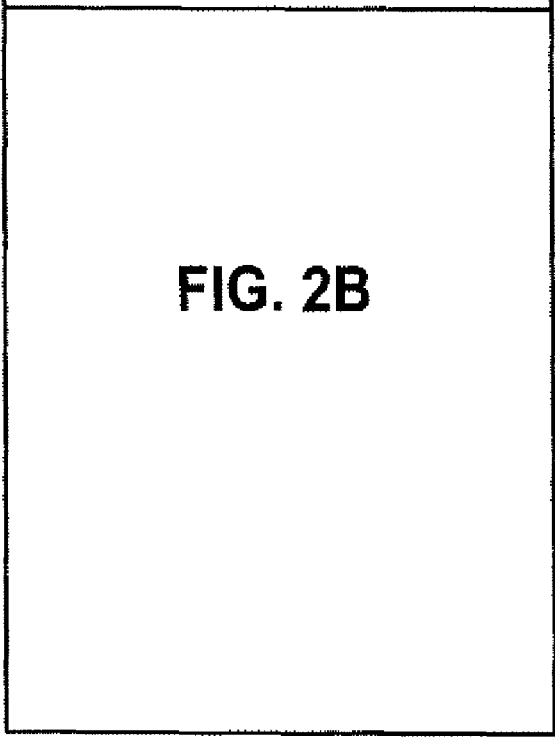
Figure 2A:
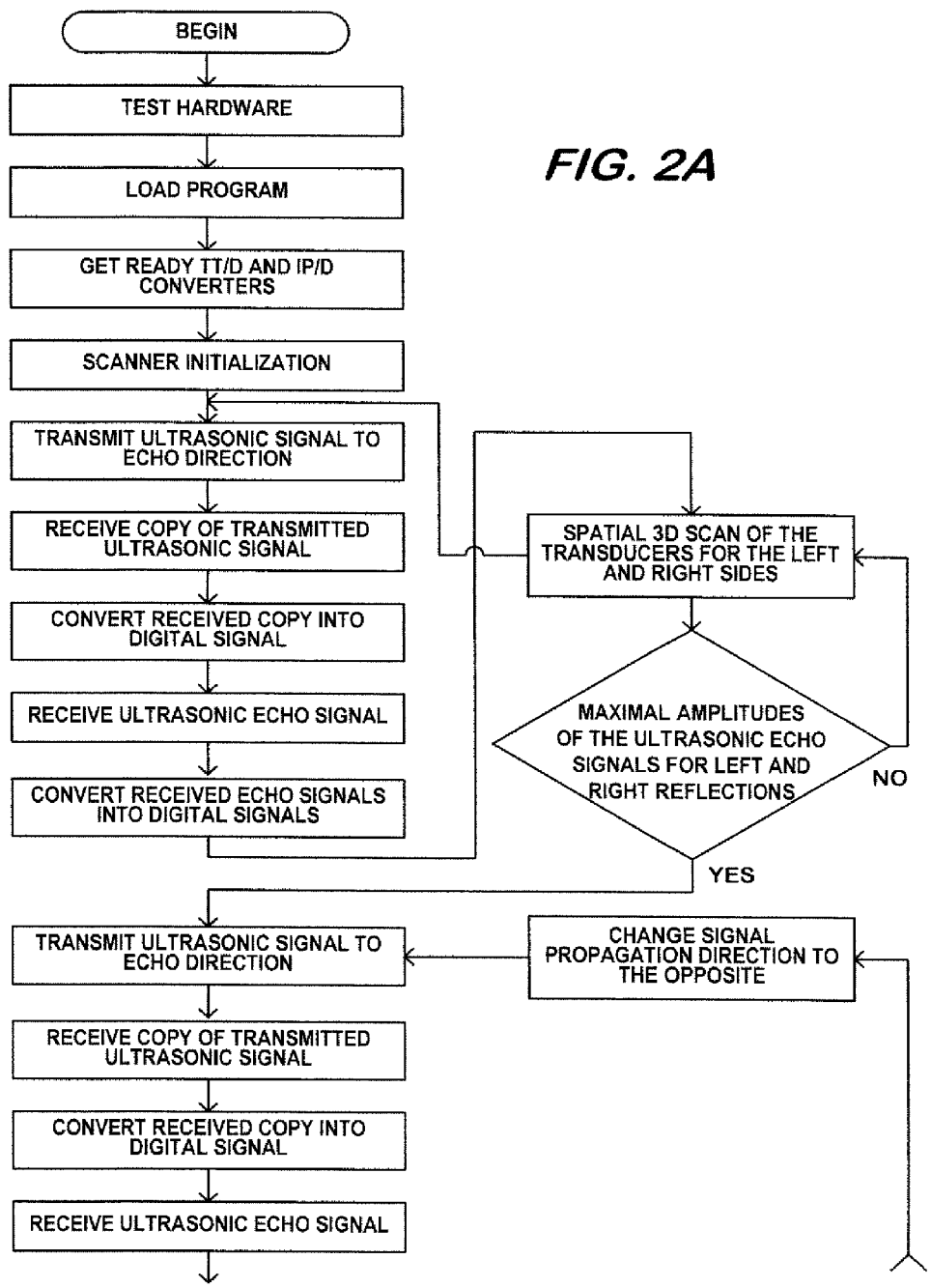
Figure 2B:
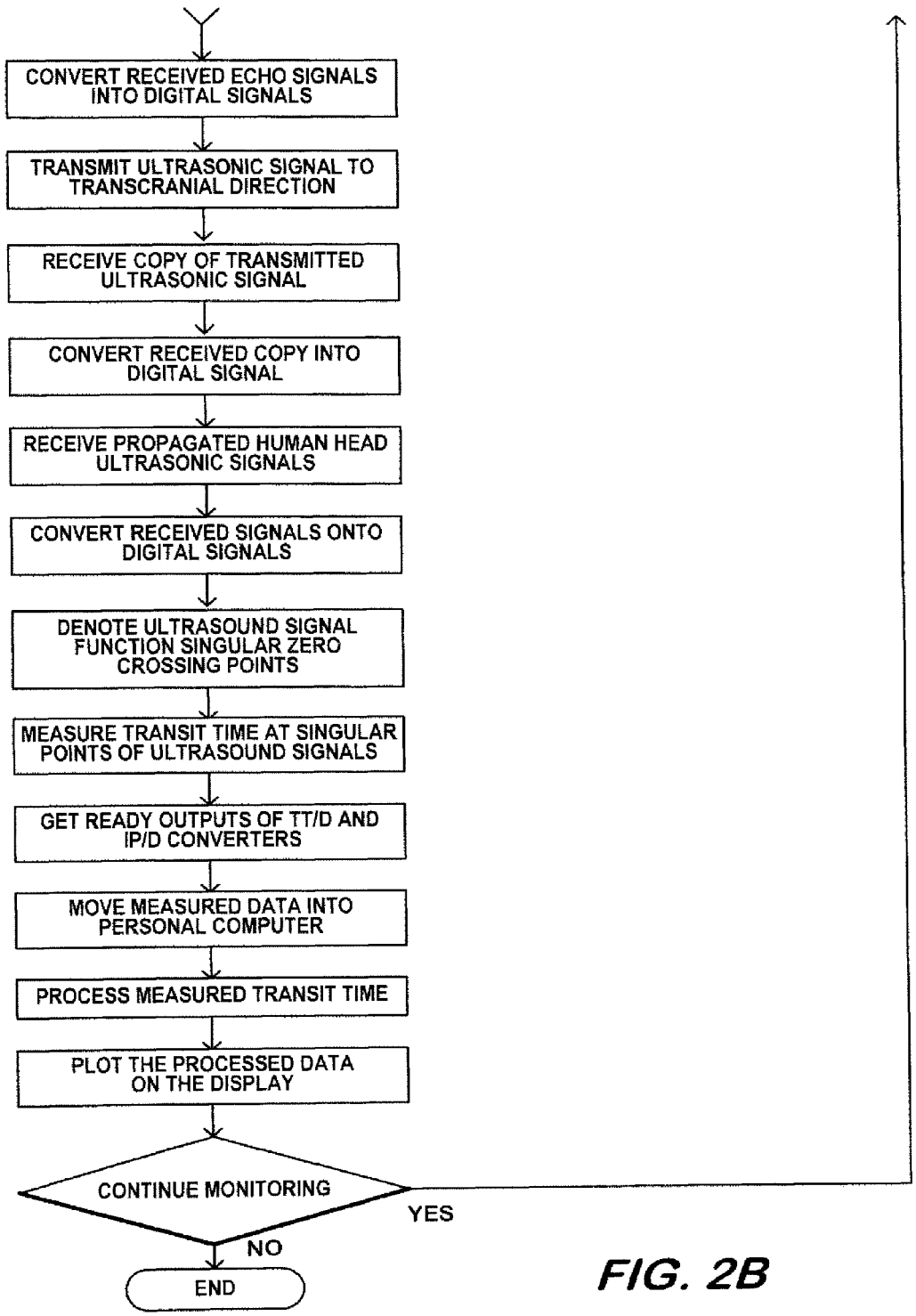

In FIG. 2, an algorithm of one advantageous method and apparatus according to the present invention is shown.

Figure 3:
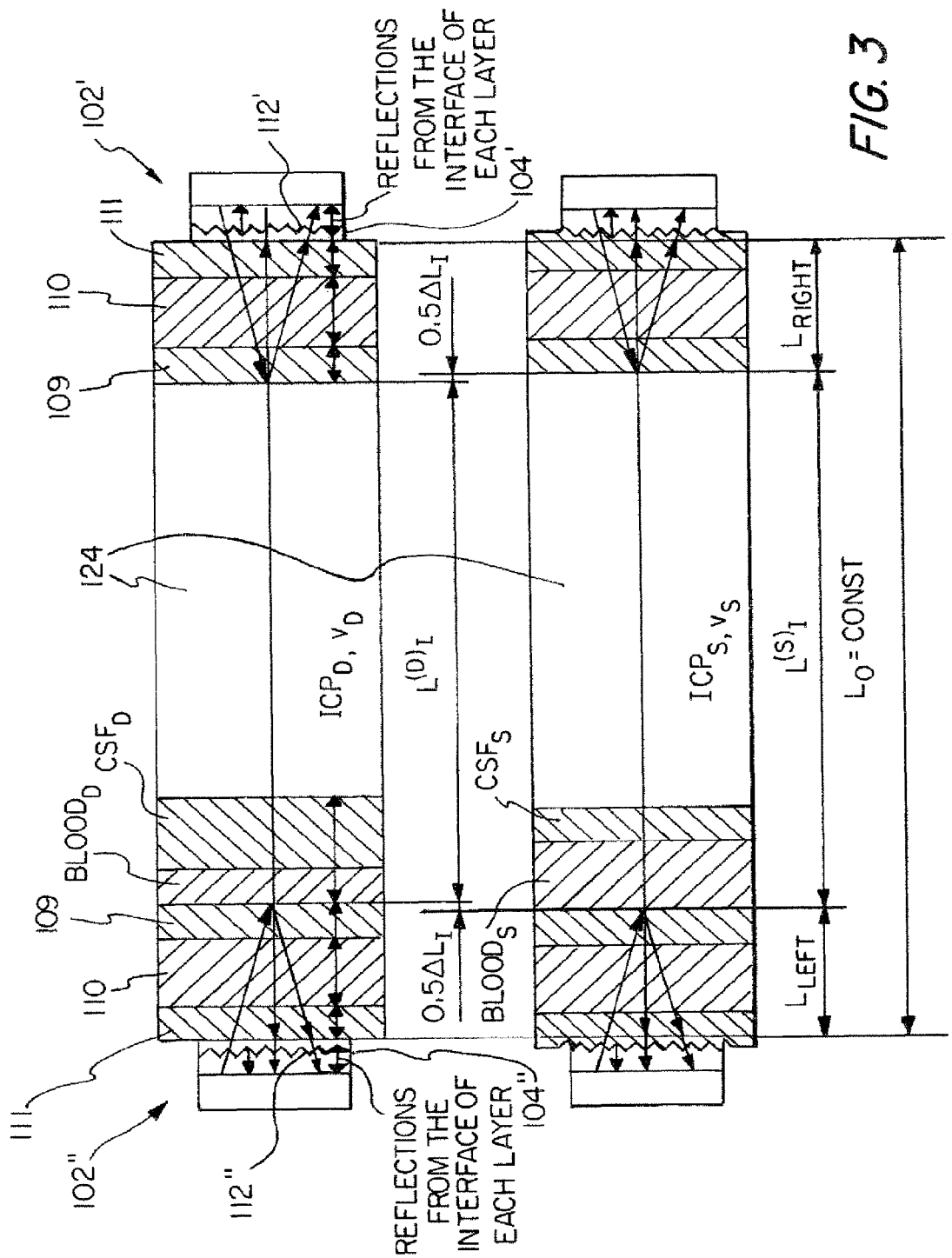
FIG. 3 is a diagram of the internal structure of parenchymal acoustic path in accordance with FIG. 1.

FIG. 3 is a diagram of the internal structure of parenchymal acoustic path 124 in accordance with one embodiment of the invention. The upper diagram of FIG. 3 illustrates the internal structure in the diastolic moment of cardiac pulsation and the lower diagram illustrates the systolic moment of cardiac pulsation. Ultrasound gel pad layers 104', 104" in FIG. 3 have a triangular reflecting surface 112', 112" in order to get the same direction of reflected ultrasound beam from that reflecting surface as the direction of the transmitted ultrasound beam. Due to the triangular reflecting surface 112', 112" the echo signal from the gel pad layers has the same amplitude independently on the transmission direction. It allows the system to achieve a better signal to noise ratio than if the reflecting surface and ultrasound beam are perpendicular.

As shown in FIG. 1, each ultrasonic transmitting/receiving transducer 102', 102" may be provided as a hybrid ultrasonic transducer (HT) having a main 2.0 MHz wide band ceramic ultrasonic transducer (MT) which comprises a piezoceramic disc 114 and ring 116 (FIG. 14) and a super wide band (greater than 10.0 MHz) polyvinylidene fluoride piezoelectric film (PVDF) ultrasonic transducer 118. The PVDF transducer 118 is placed between the ultrasound gel pad 104 and the main ultrasonic transducer 102 (FIG. 3). In this case the ultrasonic pulses transmitted by the main transducer 102 pass through PVDF transducers 118 practically without attenuation. At the output of the PVDF transducer 118, in this embodiment, are electric pulses—copies of the transmitted ultrasonic pulses and copies of the ultrasonic echo pulses, which pass twice through the external tissues 111, skull bones 110 and dura matter 109. These ultrasonic pulses are received by PVDF transducers 118', 118" on both sides of the human head 60 because of the time division multiplexing of the ultrasonic pulse transmission directions. These directions are changed to the opposite 500 times per second by the time division multiplexer 120 (FIG. 1), which is coupled to a timing generator 150. The period of the human head insonation is fixed at 1000 Hz by reference clock 122, which is coupled to multiplexer 120 via a transmitter 152 (FIG. 1). The time-of-flight determination errors caused by frequency dependent ultrasound velocities in the external tissues 111, skull 110 and intracranial media 109 are eliminated by including super wide band PVDF transducers 118', 118" into hybrid ultrasonic transducers and by application of signals with the same spectrum for propagation through the human head 60 and for propagation through the external tissues 111 and skull 110 applying the echo method. Known methods for simultaneous measurement of time-of-flight in external tissues 111, skull bone 110 and dura matter 109 together with time-of-flight measurement in the human head are based on frequency division multiplexing of echo channel and direct transmission channel. It is impossible to eliminate the errors caused by frequency dependent ultrasound velocities when different frequency ultrasonic signals are used in the known cases.

The parenchymal acoustic path 124 (PAP) is used for human head insonation. This path 124 (FIG. 3) crosses the brain parenchyma tissue without the cerebroventricles and relatively big cerebral vessels inside. The brain blood volume inside this path 124 depends on the state of dilation or constriction (or the cerebral blood flow autoregulation state) of the brain arterioles and aucillary vessels and on the state of compression by ICP of the brain venules and bridging veins. This brain blood volume is determined by measuring the transintracranial time-of-flight (TTF) of ultrasonic pulses propagated through the intracranial media. The TTF changes mainly depend on the brain blood volume because the ultrasound velocity $v_B$ is greater in the blood as compared to the ultrasound velocity $V_{PT}$ in the brain parenchyma tissue and the ultrasound velocity $V_{CSF}$ in the cerebrospinal fluid (See Table 1).

Intracranial parenchyma volume (IPV) changes are determined by the measurement of the internal period (IP) of ultrasonic pulses propagated through the intracranial media because the parenchyma tissue volume occupies more than 80% of the parenchymal acoustic path total volume. The attenuation of ultrasound in the parenchyma tissue (Table 1) is much greater than in the blood or CSF.

The main technical parameters of computer based apparatus include:

- central frequency of transmitted ultrasonic pulses spectrum—2.0 Mz;
- duration of transmitted ultrasonic pulses 800 ns at the level 0.5 of envelope and its repetition frequency 1.0 kHz;
- acoustic output parameters: derated spatial-peak, temporal-average intensity $I_{SPTA3}$=25+/−2.2 mW/cm$^2$ derated spatial-peak, pulse-average intensity $I_{SPPA3}$=1+/−0.09 W/cm$^2$;
- ultrasonic power $W_0$=1.8 mW;
- resolution of measured time-of-flight or ultrasound velocity relative values 1.25E-6 at the bandwidth of non-invasive intracranial pressure/volume pulse waves measuring channel from 0 Hz until 12 Hz; and
- resolution of measured intracranial parenchyma volume changes inside the parenchymal acoustic path less than 0.5% within all physiological region of standard intracranial pressure/volume relationship.

Figure 4:
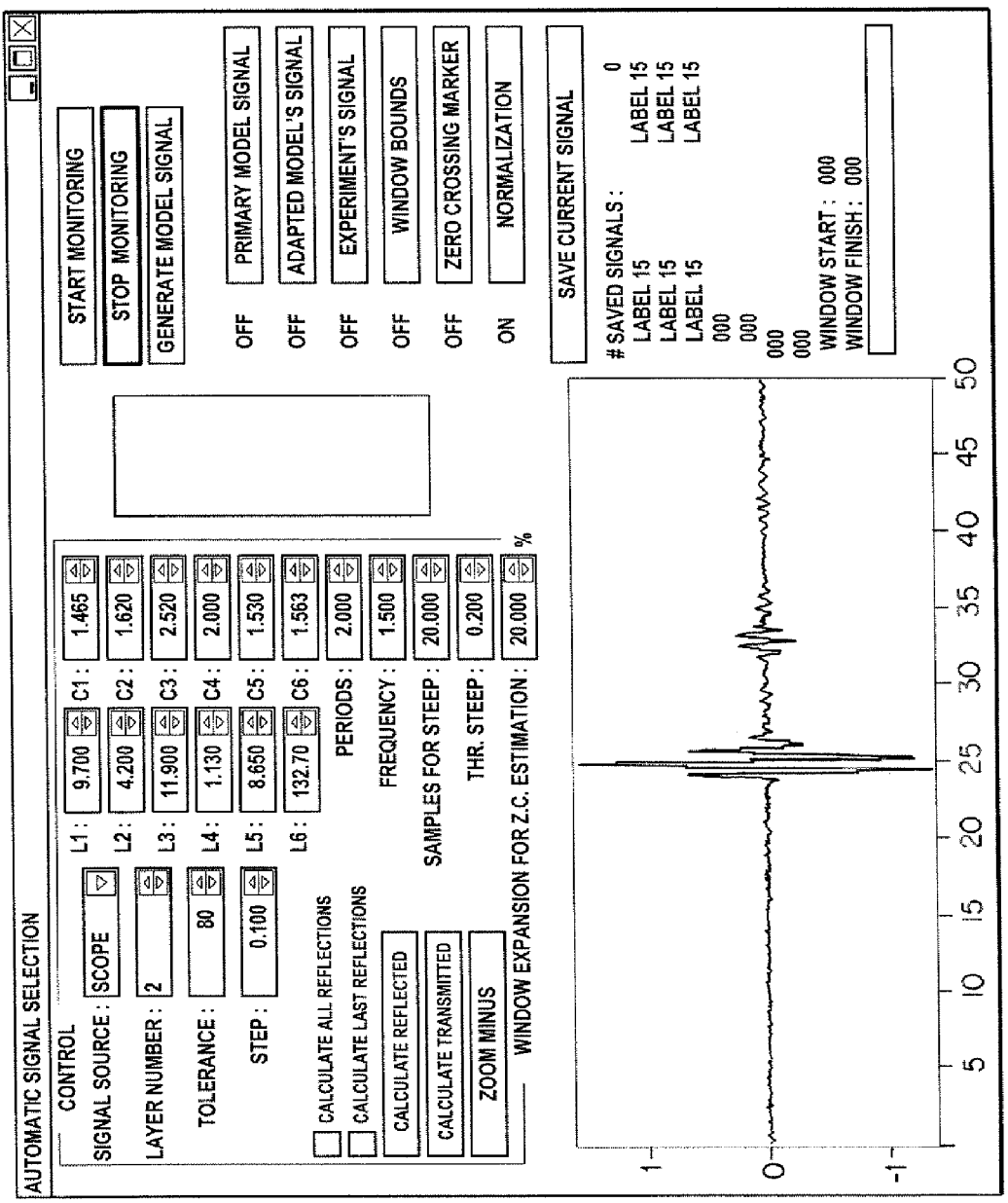
FIGS. 4-10 are screen shots according to the embodiment of FIG. 1.
Figure 5:
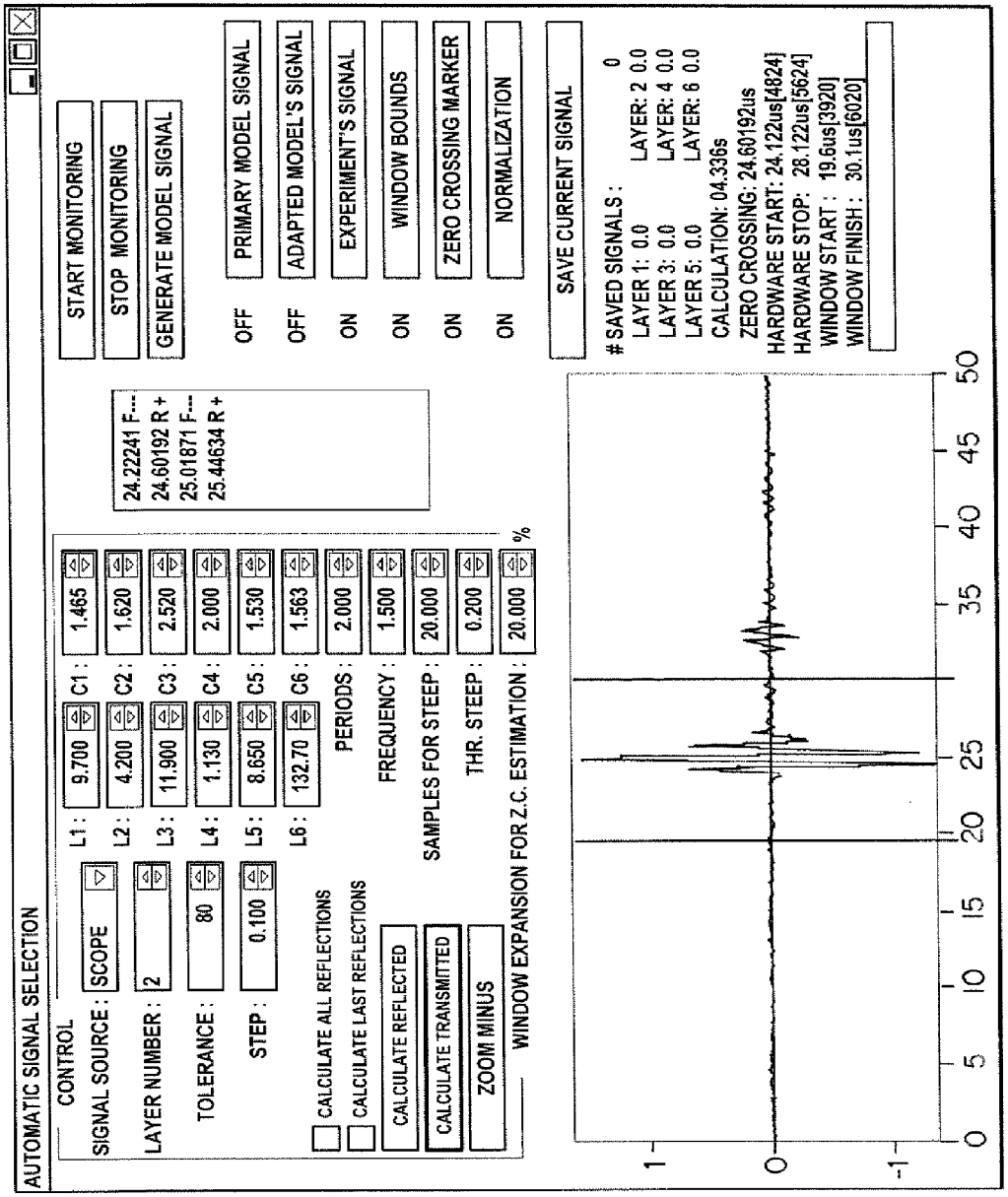
Figure 6:
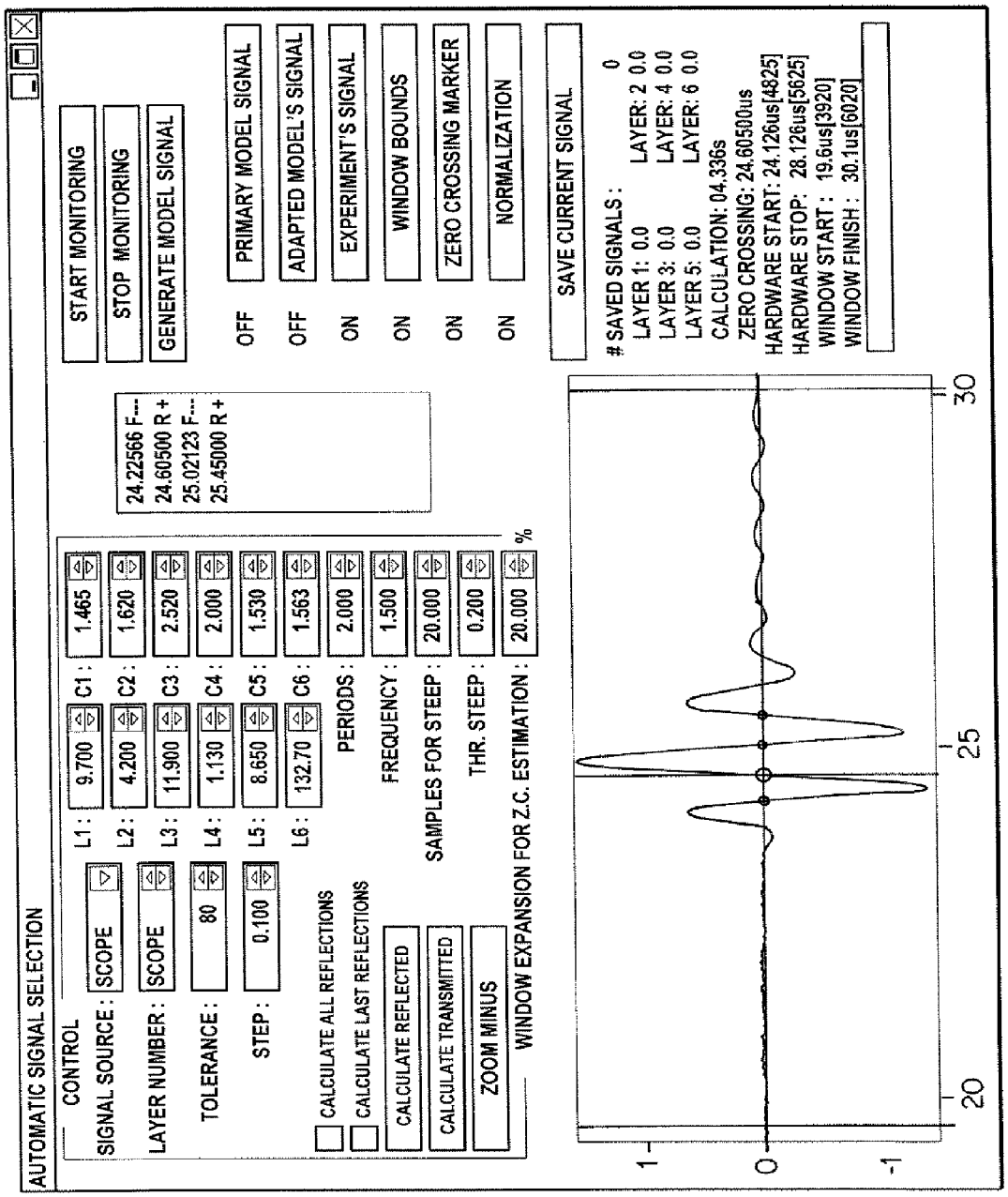

FIGS. 4-6 show the transmitted and received ultrasonic signals display windows illustrating the automatic procedures of the received signal (FIG. 4) amplitude normalization, informative signal's selection in time (FIG. 5), and identification of signal function zero crossing points (FIG. 6). The operation of the system 50 (FIG. 1) is illustrated in FIG. 3. The algorithm of operation is given in FIG. 2.

The following abbreviations are used in FIG. 3: $Blood_D$ is the total diastolic blood volume inside the parenchymal acoustic path 124, $CSF_D$ is the total diastolic CSF volume inside the same path, $ICP_D$ is the diastolic value of ICP pulse wave, $v_D$ is the diastolic value of ultrasound velocity in the parenchymal acoustic path 124, $L^{(D)}_I$ is the diastolic value of the distance between internal surfaces of dura matter 109, $L^{(S)}_I$ is the systolic value of the distance between internal surfaces of dura matter 109, $\Delta L_I$ is the difference between $L^{(S)}_I$ and $L^{(D)}_I$, and $L_0$ is the constant distance between the ultrasonic transducers 102', 102" fixed by a mechanical frame 108. The subscripts S in FIG. 3 indicate the systolic values.

It follows from FIG. 3 that systolic blood volume is increased as compared to diastolic blood volume, systolic CSF volume is decreased and parenchymal tissue volume is almost unchanged inside the parenchymal acoustic path. CSF volume is decreased because of the CSF pulsatile outflow into the spinal channel. It is also possible that the systolic intracranial distance $L^{(S)}_I$ can be a little bit bigger than the diastolic distance $L^{(D)}_I$ because of the skull displacement caused by systolic ICP increment ($ICP_S$>$ICP_D$). It follows from FIG. 3 that in case of systole $v_s$>$v_D$ because the ultrasound velocity in the wider blood layer is bigger than in the diastolic case. The result is that systolic time-of-flight $TTF_S$ is less than diastolic $TTF_D$. The other result is that the amplitude of TTF pulse wave caused by ICP pulse wave will be negative. The amplitude of TTF pulse wave is determined as $TTF_S-TTF_D$.

From FIG. 3 it also follows that the time-of-flight through external tissues 111 (TEC), skull bones 110, and dura matter 109 (TC) is measured applying echoes from the internal surface of dura matter on the left and right sides of the human head. The transintracranial time-of-flight (TTF) can be determined in this case as:

$$TTF=TF-(TEC+TC)_R-(TEC+TC)_L-T_0 \quad \text{Formula 9}$$

where TF is the time-of-flight between left and right hybrid ultrasonic transducers (FIG. 3), and To is the instrumental delay time of signals in the circuits of transmitter 152, connecting cables, hybrid ultrasonic transducers and receiver 154 (FIG. 1). In the present invention, the echo method is used and echo signals are received after propagating twice through the external tissues 111, skull bones 110, and dura matter 109. Also the direction of propagation between the two ultrasonic transducers is periodically inverted. That is why in our method, the TTF is calculated in the computer as:

$$TTF=0.5(TF_1+TF_2)-0.5(2(TEC+TC)_R+2(TEC+TC)_L)-0.5(T_{01}+T_{02}) \quad \text{Formula 10}$$

where subscripts 1 and 2 mean the opposite directions of ultrasound propagation. All time-of-flight values are measured in real time by time-of-flight to digit converter 126 (TT/D, FIG. 1). To measure these values, the time windows are used for every single pulse (FIG. 4). These time windows are used for the selection of the same zero crossing point of signal functions where the slope of signal function is maximal (FIG. 4). The width of time selection windows is chosen less than the half of every signal's internal period (IP). Only one zero crossing point of signal function is selected for time-of-flight measurements in this case. In the case of internal period (IP) measurement, the separate internal period to digit (IP/D) converter is used (FIG. 1). The real time time-of-flight and internal period simultaneous measurement data are transmitted to the computer 100 (FIG. 1) for filtering, calculations, displaying, and saving.

The instrumental delay times $T_{01}$ and $T_{02}$ are measured in real time by periodically connecting the outputs of left and right PVDF transducers 118', 118" by time division multiplexer 120 (FIG. 1). In this case the object of measurement—parenchymal acoustic path—is eliminated from the time-of-flight measurement channel and only $T_{01}$ and $T_{02}$ are measured by TT/D converter 126. The measured data is used for the calculation of TTF data. All instrumental drifts of delay times of apparatus (FIG. 1) are automatically eliminated in this case.

The ultrasound intracranial attenuation inside the parenchymal acoustic path 124 cannot be measured by applying conventional methods. First of all, it is impossible to get the necessary time resolution applying the fastest and highest resolution analog-to-digital converters 128 (ADC FIG. 1) and digital signal processors 130 (DSP FIG. 1). That is why in system 50, the IP/D converter 132 is used to measure the internal period of ultrasonic signals with high resolution up to 60 ps. The amplitude of the transmitted signal, echo signals, and propagated through the human head signals is determined by applying ADC 128, DSP 130 and the averaging up to 5000 pulses. The ultrasonic signals are virtually reconstructed in the computer 100 applying the measured data of the internal period and amplitude and also applying the Gaussian shape of the signals envelope.

The elimination of the frequency dependent attenuation in the external tissues and skull bones $\beta_L(j\omega)$ of the left side of the head and the right side of the head $\beta_R(j\omega)$ from the total attenuation data $\beta_T(j\omega)$ is carried out using the following formulas:

$$S_{EL}(j\omega) \times (\beta_{IL}(j\omega))^2 = S(j\omega) \quad \text{Formula 11}$$

$$S_{ER}(j\omega) \times (\beta_{IR}(j\omega))^2 = S(j\omega) \quad \text{Formula 12}$$

$$S_T(j\omega) \times \beta_{IT}(j\omega) = S(j\omega) \quad \text{Formula 13}$$

where S(jω) is the complex spectrum of the transmitted ultrasonic signal; $S_{EL}(j\omega)$ is complex spectrum of the echo signal from the left internal surface of dura matter; $S_{ER}(j\omega)$ is the same for the right side; $S_T(j\omega)$ is complex spectrum of the signal which passed the human head; $\beta_{IL}(j\omega)$ is complex transient function of the filter, which is inverse to the frequency dependent attenuation function $\beta_L(j\omega)$ of the left side of cranium with external tissues; $\beta_{IR}(j\omega)$ is the same for the right side; $\beta_{IT}(j\omega)$ is the same for the human head, all inverse filters marked by (I*) have the complex transient function $\beta_I(j\omega)=1/\beta(j\omega)$, were $\beta(j\omega)$ is the attenuation function of structure layer (*).

The frequency dependent transcranial attenuation of ultrasound $\beta_{TTC}(j\omega)$ from the left internal surface of dura matter 109 to the right internal surface of the dura matter 109 is calculated from:

$$\beta_{TTC}(j\omega)=(\beta_{IL}(j\omega)\times\beta_{IR}(j\omega))/\beta_{IT}(j\omega) \quad \text{Formula 14}$$

The functions $\beta_{IL}(j\omega)$, $\beta_{IR}(j\omega)$, $\beta_{IT}(j\omega$ are calculated in the computer 100 applying formulas (11), (12), (13), measured results of internal periods of signals $S(j\omega)$, $S_{EL}(j\omega)$, $S_{ER}(j\omega)$, virtually reconstructed time dependencies of these signals and fast Fourier transform (FFT). The determined value of $\beta_{TTC}(j\omega)$ is linearly proportional to the parenchyma tissue volume inside the parenchymal acoustic path.

Figure 7:
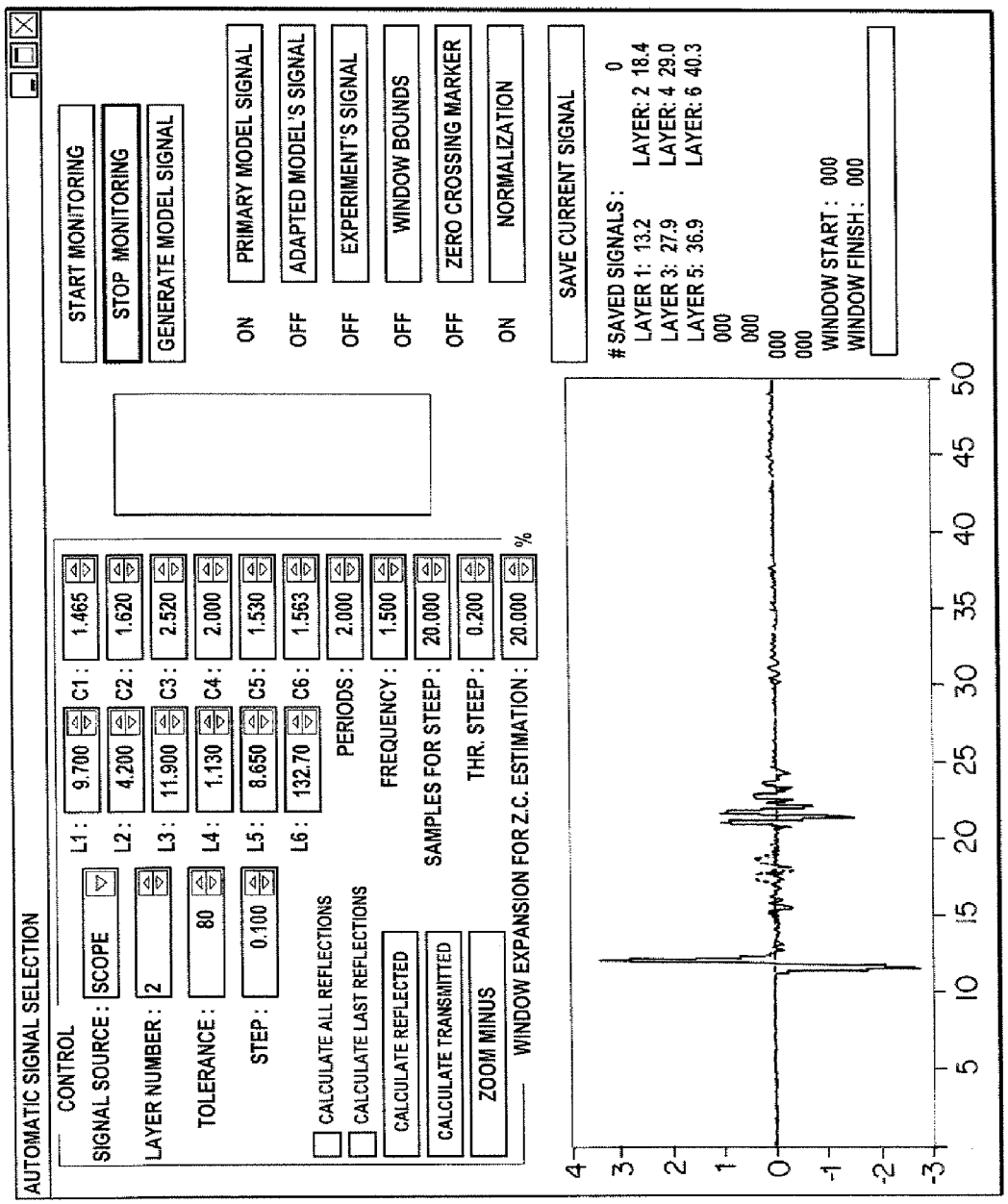

As shown in FIG. 7, the option for echo ultrasonic signal window parameters adjustment is incorporated into the monitor's software. The raw digitized signal reflected from the human skull surface is presented as is the primary simulated signal without iterative adjustment of the model parameters until the simulated response fits to the measured. This multilayered biological medium model is incorporated with a non-linear deconvolution technique, which is based on time-frequency analysis, in order to perform automatic selection and window adjustment of the appropriate reflection without necessitating intervention of an experienced operator.

Figure 8:
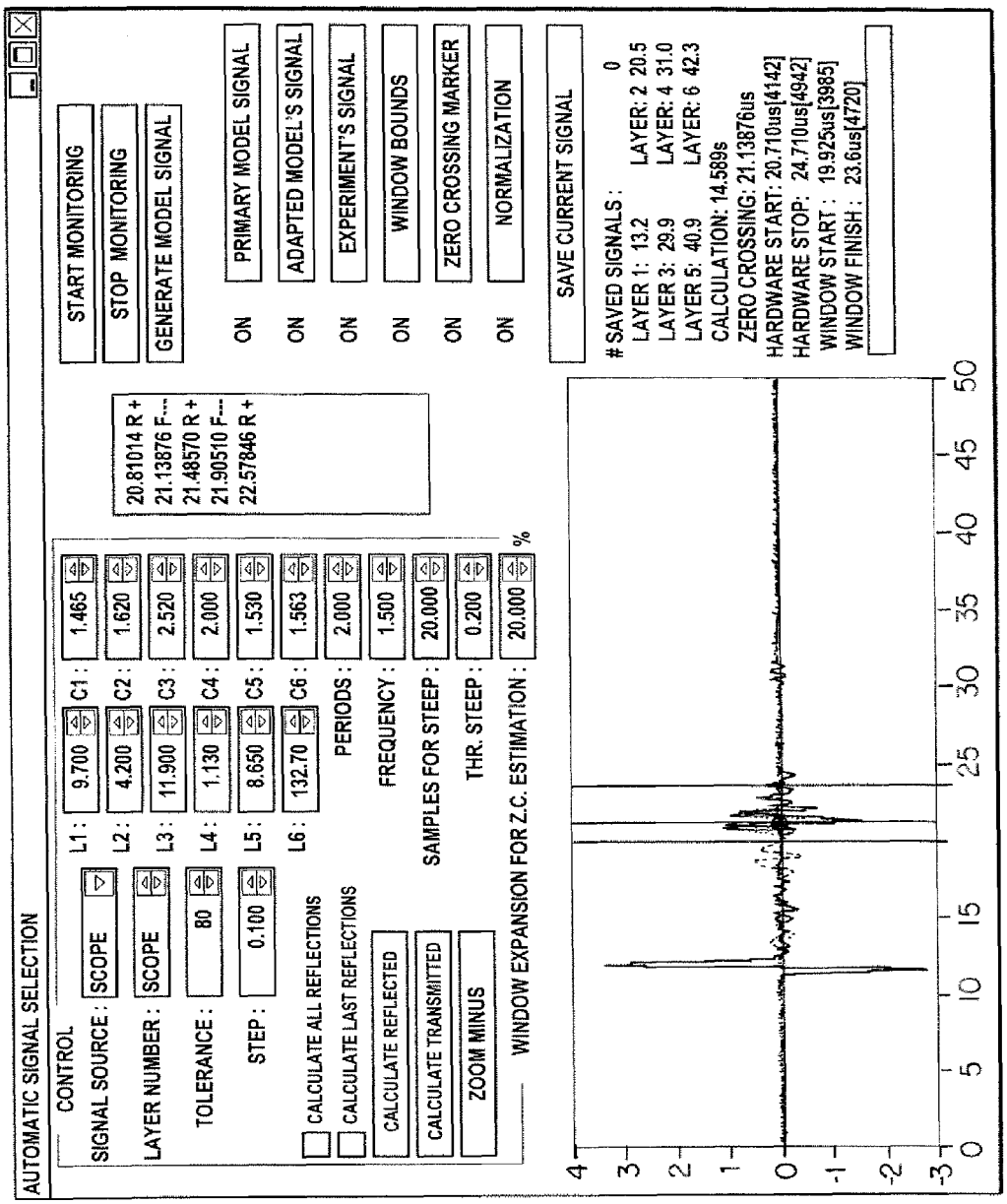

FIG. 8 is an illustration of the window parameters adjustment procedure, which has been performed for informative part of the digitized raw signal (FIG. 7). The result of the automatic adjustment is the raw digitized ultrasonic signal placed into the rectangular time window with user defined width (optionally 2 times wider than informative part of the ultrasonic signal transmitted through human cranium). Also shown is the primary simulated signal using the initial parameters of the model without iterative adjustment of the model parameters. The simulated response of the model is further shown. It is obtained by iterative adjustment of the model parameters during non-linear deconvolution and fits best to the measured signal. In such procedure the L (thickness) and C (ultrasound velocity) parameters, which describe biological medium, are evaluated for each patient individually. In such window the zero-crossing values above the threshold level of the appropriate steep of the signal slope has been evaluated. Then, on-line monitoring of the zero-crossing deviation has been started (five values of the estimated zero-crossings). The hardware for time-of-flight precise measurement for appropriate segment of the signal has been initiated by the event, which starts from 100 ns earlier than the beginning of the first zero-crossing value and ends after the 4 ps.

Figure 9:
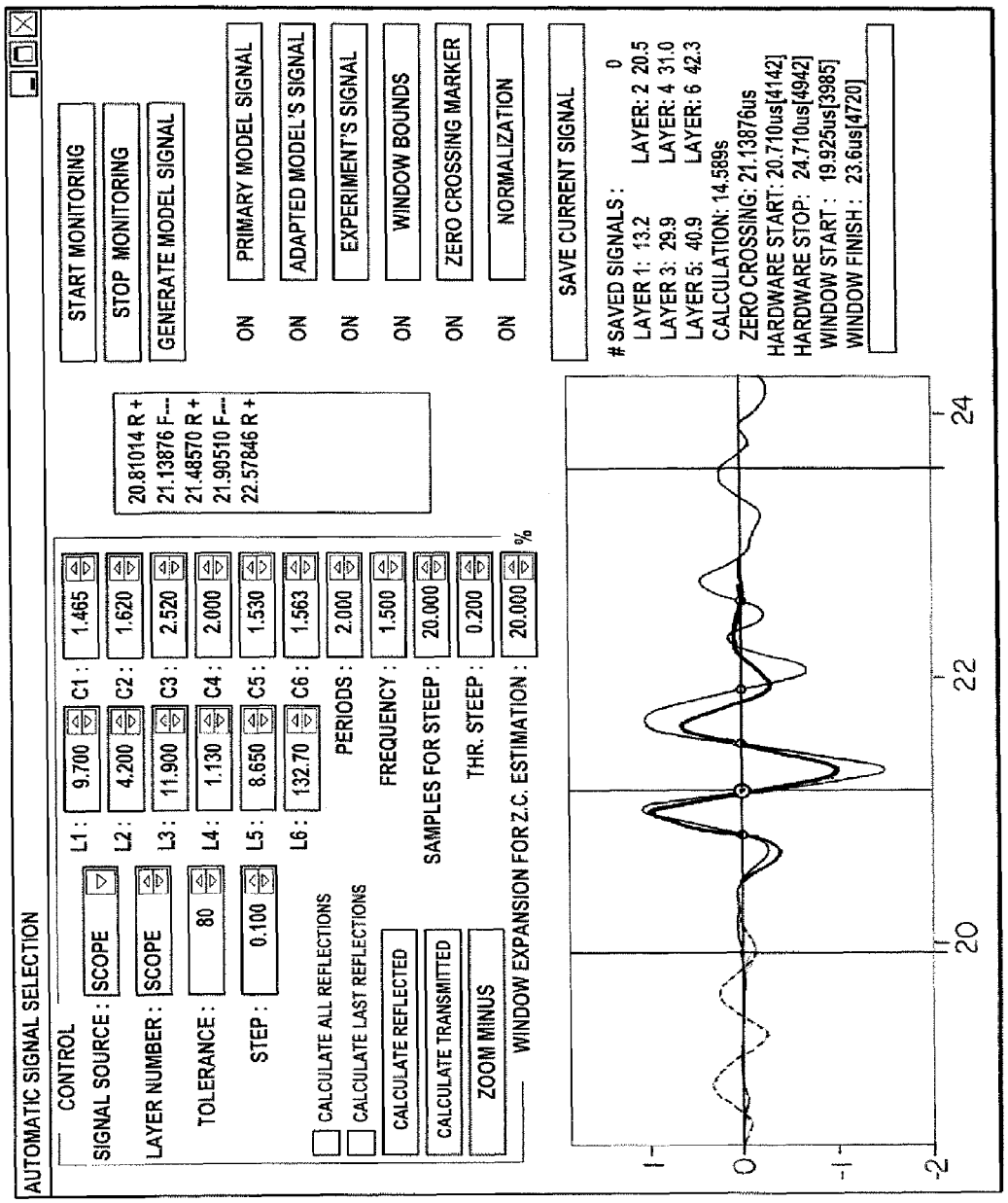

FIG. 9 illustrates zoom option of the automatically adjusted digitized raw ultrasonic signal (which is reflected from the particular interface from human cranium, for example between the skull bone 110 and the dura matter 109) is also enabled. The raw digitized ultrasonic signal, the primary simulated signal without iterative adjustment of the model parameters, and the simulated response of the model obtained during iterative adjustment of the model parameters (thickness L and ultrasound velocity C) that best fit the measured signal are all presented in this figure.

Figure 10:
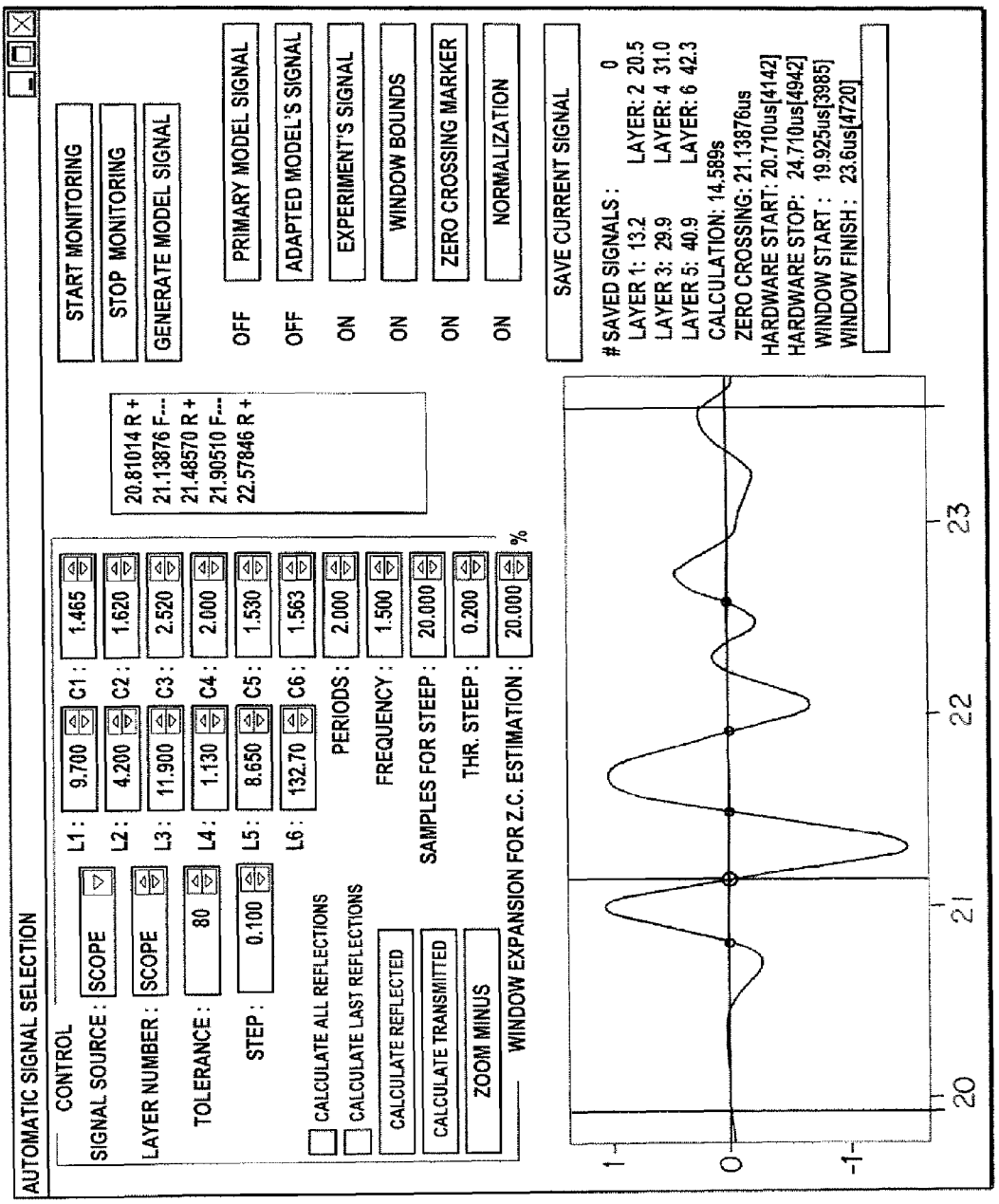

FIG. 10 illustrates zoom option of the appropriate automatically adjusted digitized raw ultrasonic signal (which is reflected from human skull 110) is also enabled with turning off option of the primary and iteratively adapted simulated signals.

Figure 11A:
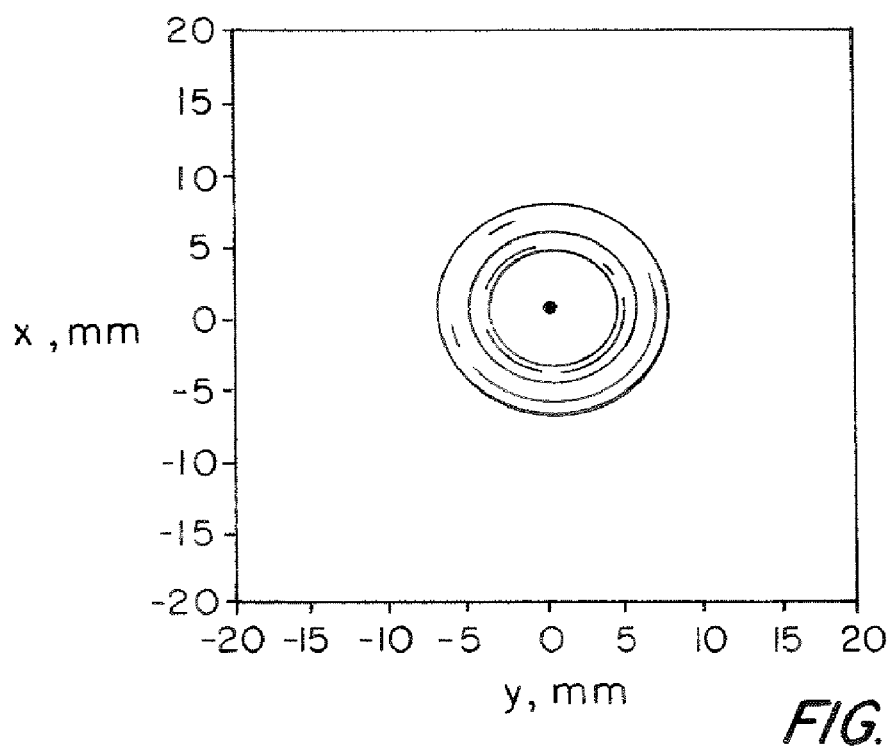
FIGS. 11a and 11b are data graphs for simulated acoustic fields according to the embodiment of FIG. 1.
Figure 11B:
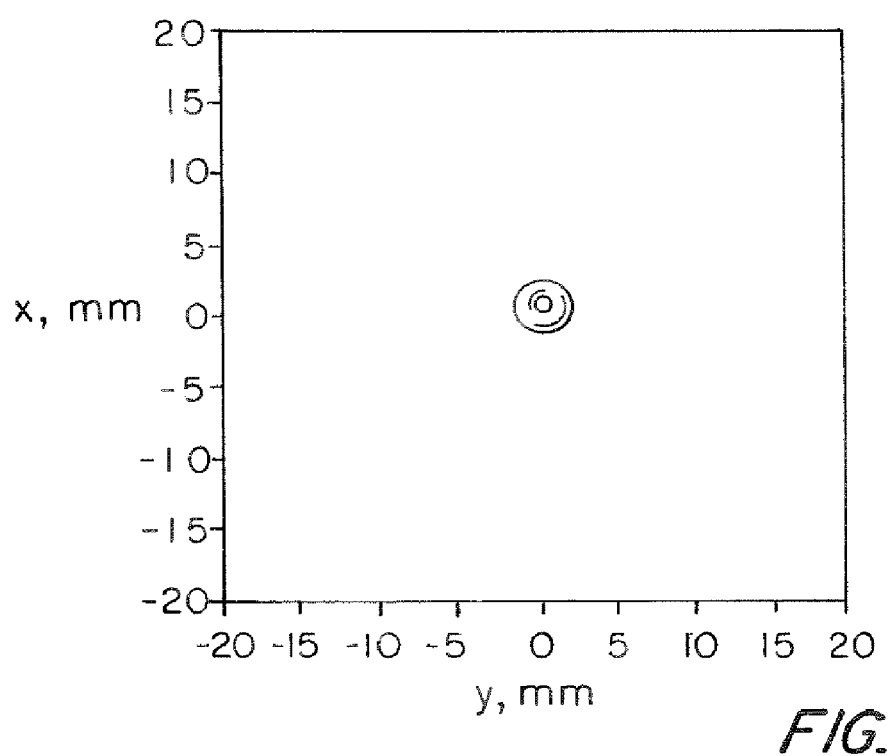

FIGS. 11a and 11b illustrate simulated acoustic fields in a pulse-echo mode from the point type reflector placed at the distance 15 mm away from the surface of the of the hybrid double action disc and ring type ultrasonic transducer (in the medium of ultrasound gel pad 104 "Aquaflex"). In 11a, the composite ring 114 (outer D=16 mm) and the composite disc 116 (D=5 mm) are acting simultaneously. In 11b, only the composite disc 116 is acting (D=5 mm).

Figure 12:
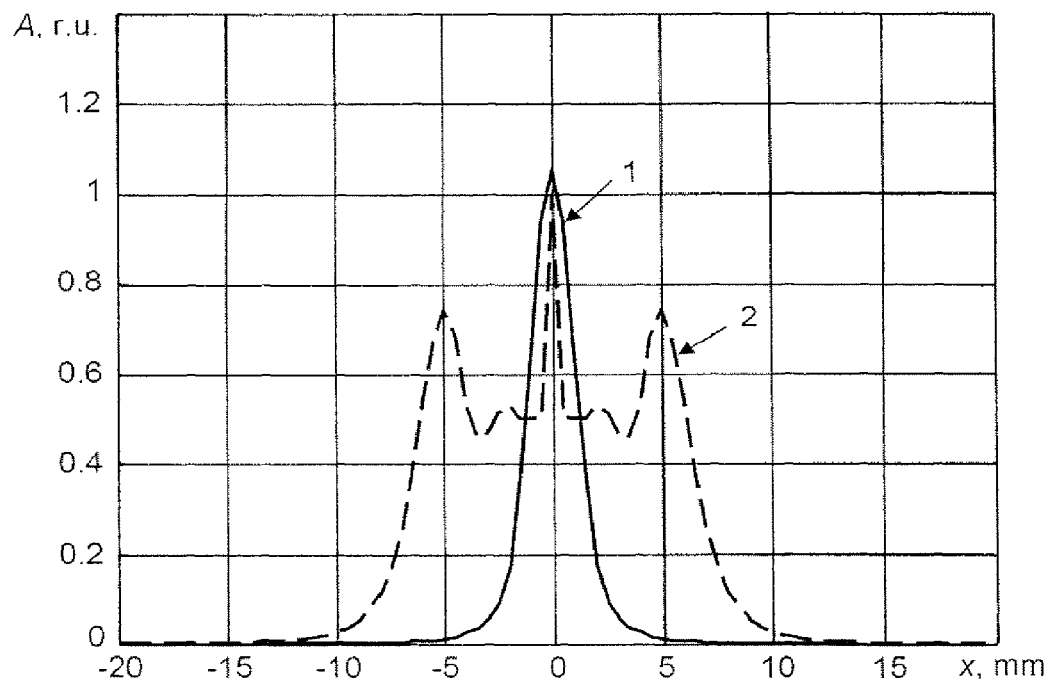
FIG. 12 is a data graph illustrating normalized distributions of the simulated acoustic fields according to the system of FIG. 1.

FIG. 12 shows the normalized distributions (parallel to the surface of the transducer) of the simulated acoustic fields in a pulse-echo mode at the distance 15 mm away from the surface of the hybrid double action disc 114 and ring 116 ultrasonic transducer: 1—composite disc (D=5 mm) is presented in solid line, 2—composite disc (D=5 mm) acting simultaneously with the composite ring (outer D=16 mm) is presented in dashed line. The uniform structure of the acoustic field in a pulse-echo mode for segment of the hybrid double action ultrasonic transducer having smaller diameter (composite disc 114 with diameter D=5 mm) is clearly seen. A, r.u. denotes the amplitude in relative units.

Figure 13:
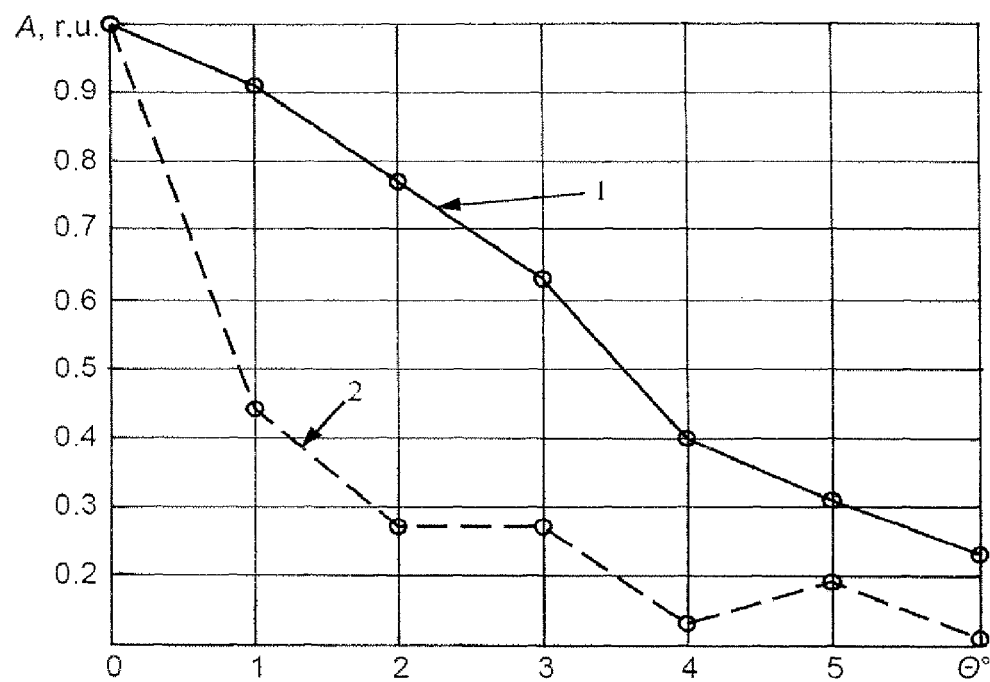
FIG. 13 is a data graph of normalized peak-to-peak amplitudes of the received experimental signals versus deflection angle of the hybrid double action ultrasonic transducer according to the system of FIG. 1.

FIG. 13 illustrates the normalized peak-to-peak amplitudes of the received experimental signals (in a pulse-echo mode) versus deflection angle of the hybrid double action ultrasonic transducer away from the normal incidence to the planar surface mimicking skull bone (at the distance 15 mm away from the transducer surface): 1—composite disc (D=5 mm), 2—composite disc (D=5 mm) acting simultaneously with the composite ring (outer D=16 mm). The presented figure indicates efficiency of the smaller segment of the hybrid double action ultrasonic transducer acting in a pulse-echo mode in the case of the reflection from the skull bone surface due to short distance of the far field zone.

Figure 14A:
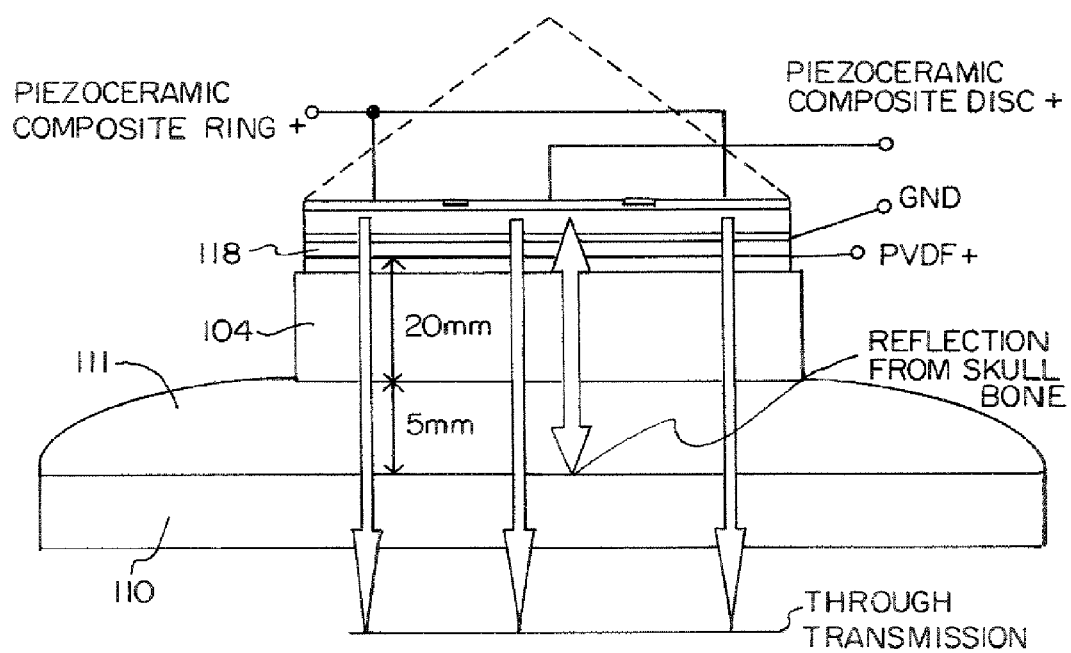
FIGS. 14a and 14b illustrate the hybrid double action disc and ring type ultrasonic transducer according to FIG. 1.
Figure 14B:
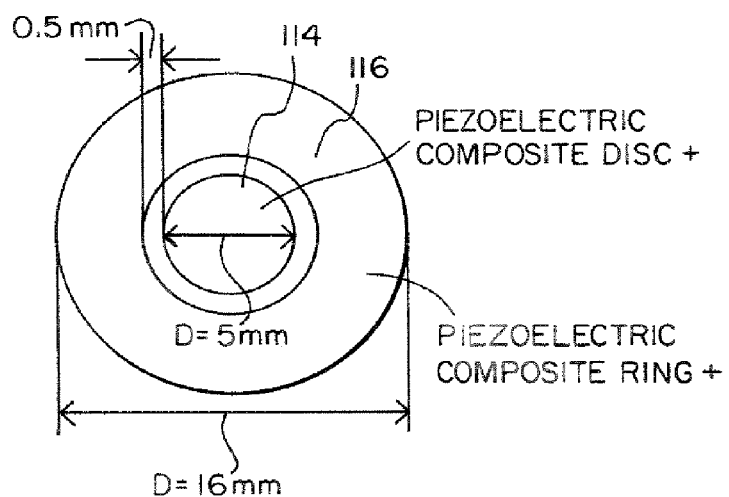

FIGS. 14a and 14b illustrate the hybrid double action disc 114 and ring 116 type ultrasonic transducer (combination between composite disc and composite ring) with two switchable different distances of the far field zone: 14a—front side view, 14b—top side view (from the side of the active electrodes). The piezoceramic disc 114 is used as a single element in order to obtain a reflection from the skull bone 110 surface. Additionally, the disc 114 can be used simultaneously with the piezoceramic ring 116 in the case of transmission through the human head 60.

Figure 15:
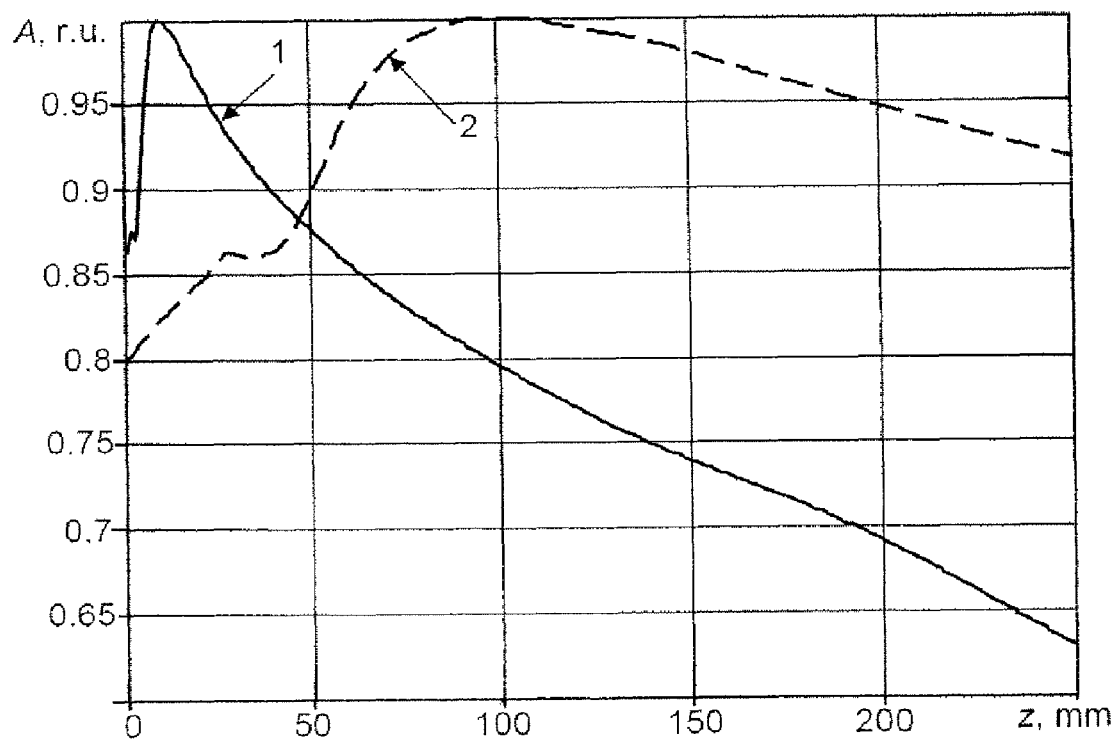
FIG. 15 is a data graph of normalized distributions of the simulated acoustic fields according to the system of FIG. 1.

FIG. 15 illustrates normalized distributions of the simulated acoustic fields in a pulse mode along the acoustic axis of the hybrid double action ultrasonic transducer (the distance of the far field zone is clearly seen): 1—composite disc (D=5 mm) is presented in solid line, 2—composite ring (outer D=16 mm) acting simultaneously with the composite disc (D=5 mm) is presented in dashed line. A, r.u. denotes the amplitude in relative units.

Figure 16:
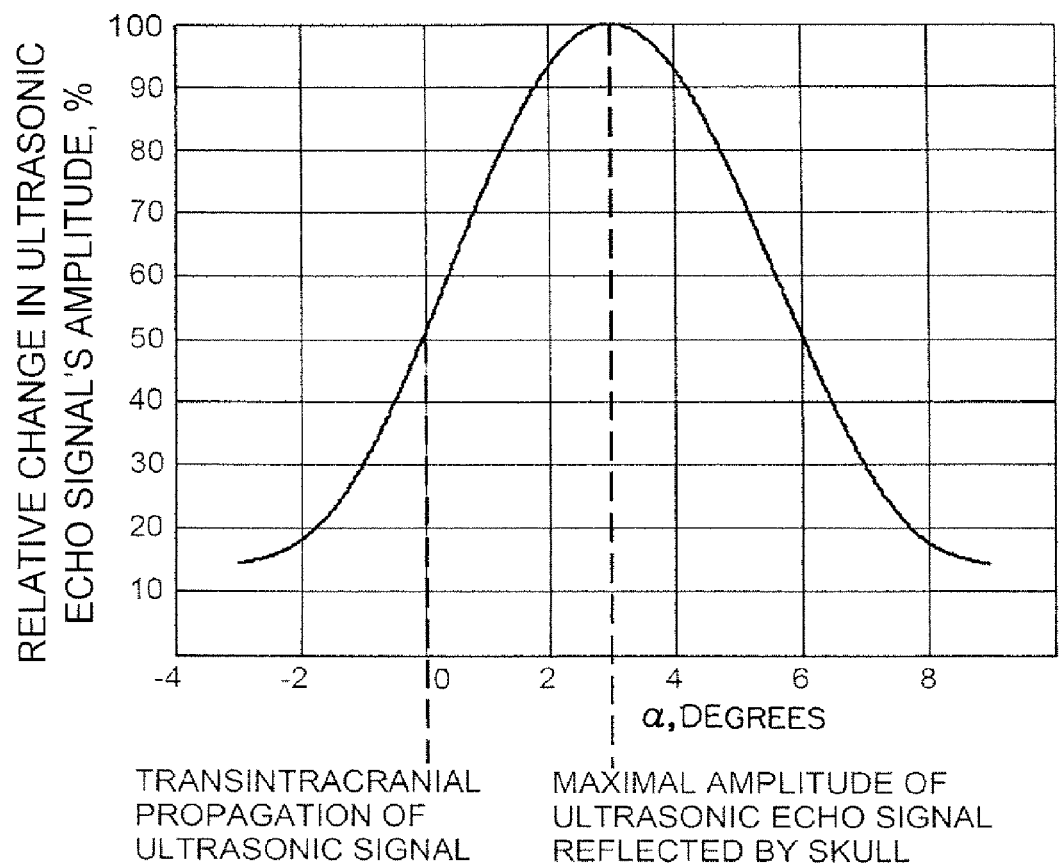
FIG. 16 is a data graph of the relative change of ultrasonic echo signal's amplitude depending on the skull surface insonation angle $\alpha$ according to the system of FIG. 1.

FIG. 16 illustrates a relative change of ultrasonic echo signal's amplitude depending on the skull surface insonation angle α. It is shown that maximal amplitude of the ultrasonic echo signal reflected by the skull at the optimal insonation direction (plus 3 degrees) is twice as high as the amplitude at the zero degree direction (direction of transintracranial propagation).

Figure 17:
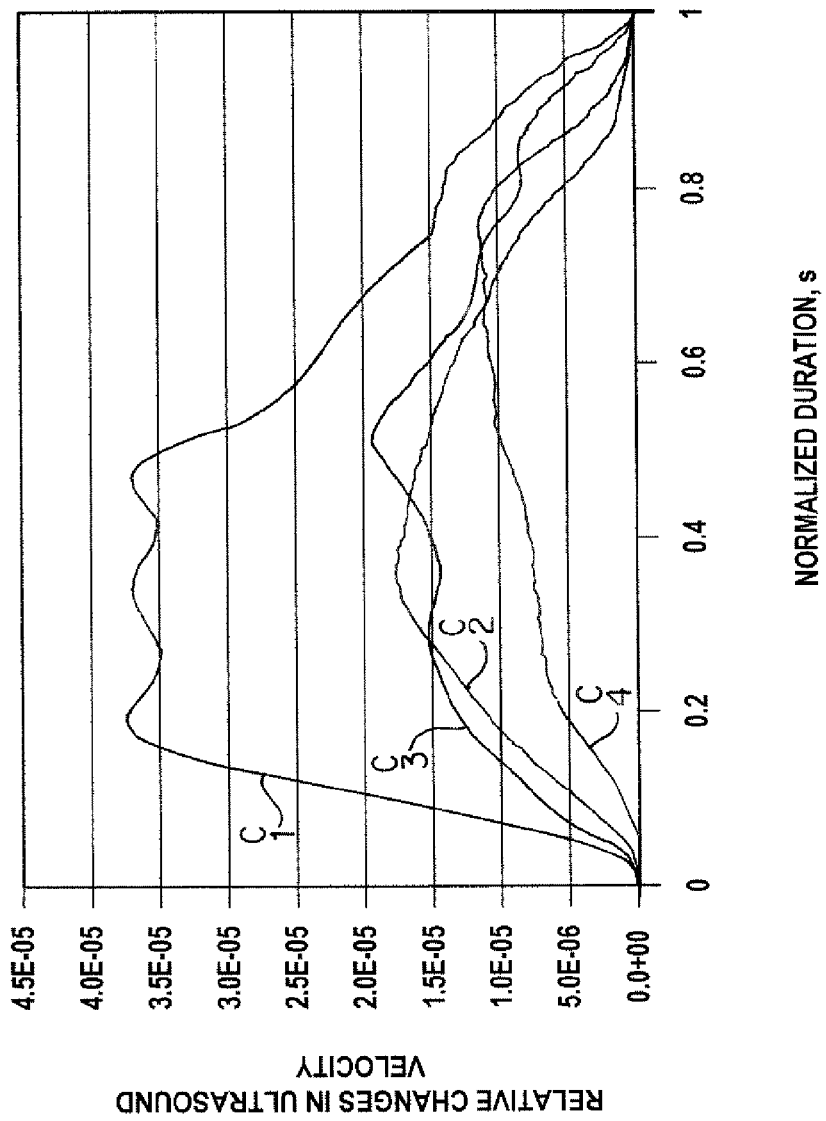
FIG. 17 is a data graph illustrating non-invasively measured intracranial volumetric pulse waves (VPW) at different intracraniospinal compliances C according to the system of FIG. 1.

FIG. 17 illustrates non-invasively measured intracranial volumetric pulse waves (VPW) at different intracraniospinal compliances C (compliance measured invasively and simultaneously with non-invasive measurement). In this figure, $C_1=1.08$, $C_2=0.62$, $C_3=0.43$, and $C_4=0.25$. The Spiegelberg (Germany) invasive monitor was used for invasive compliance measurements on intensive care unit patients in coma. The Vittamed (Lithuania—USA) non-invasive monitor was used for non-invasive VPW measurements.

Figure 18:
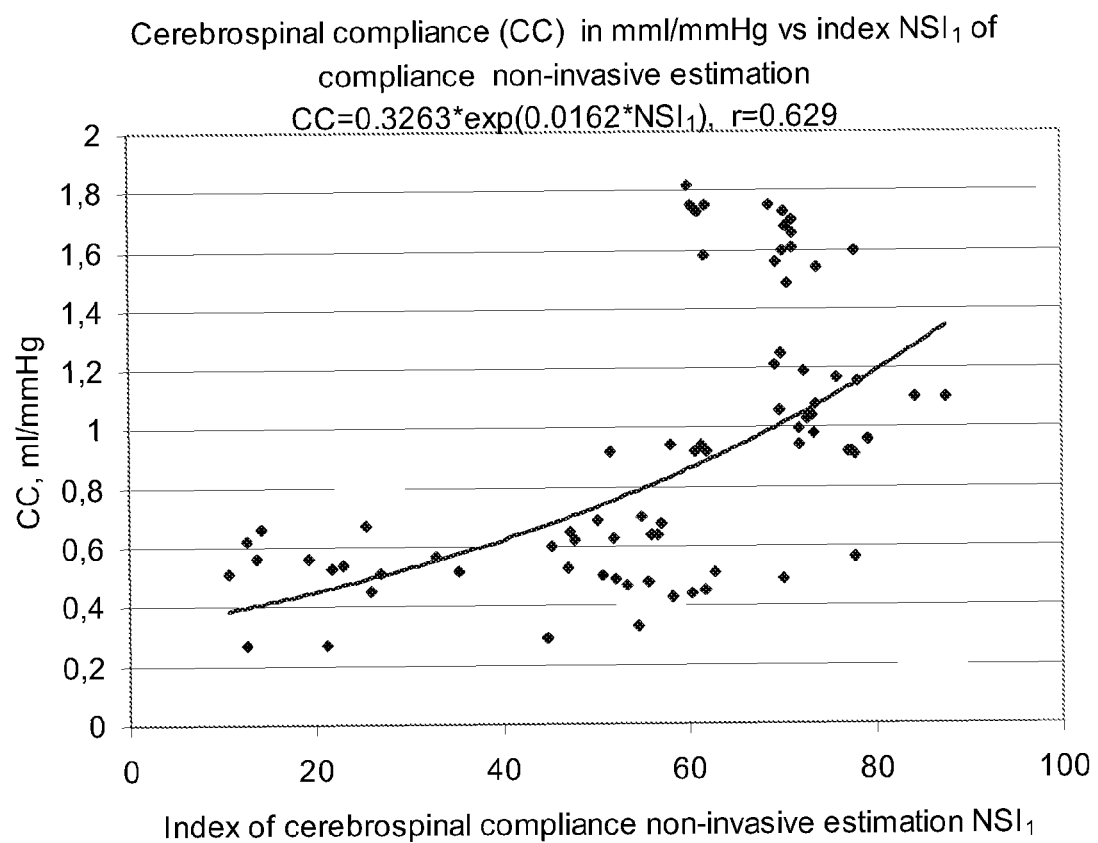
FIG. 18 illustrates the changes of brain compliance due to the pathological changes in intracranial component volumes influences the cerebral blood outflow according to the system of FIG. 1.

FIG. 18 illustrates how changes in brain compliance due to pathological changes in intracranial component volumes influences cerebral blood outflow. These cerebrospinal compliance changes can be determined by measuring the parameters of cerebral blood volume pulse waves.

Figure 19A:
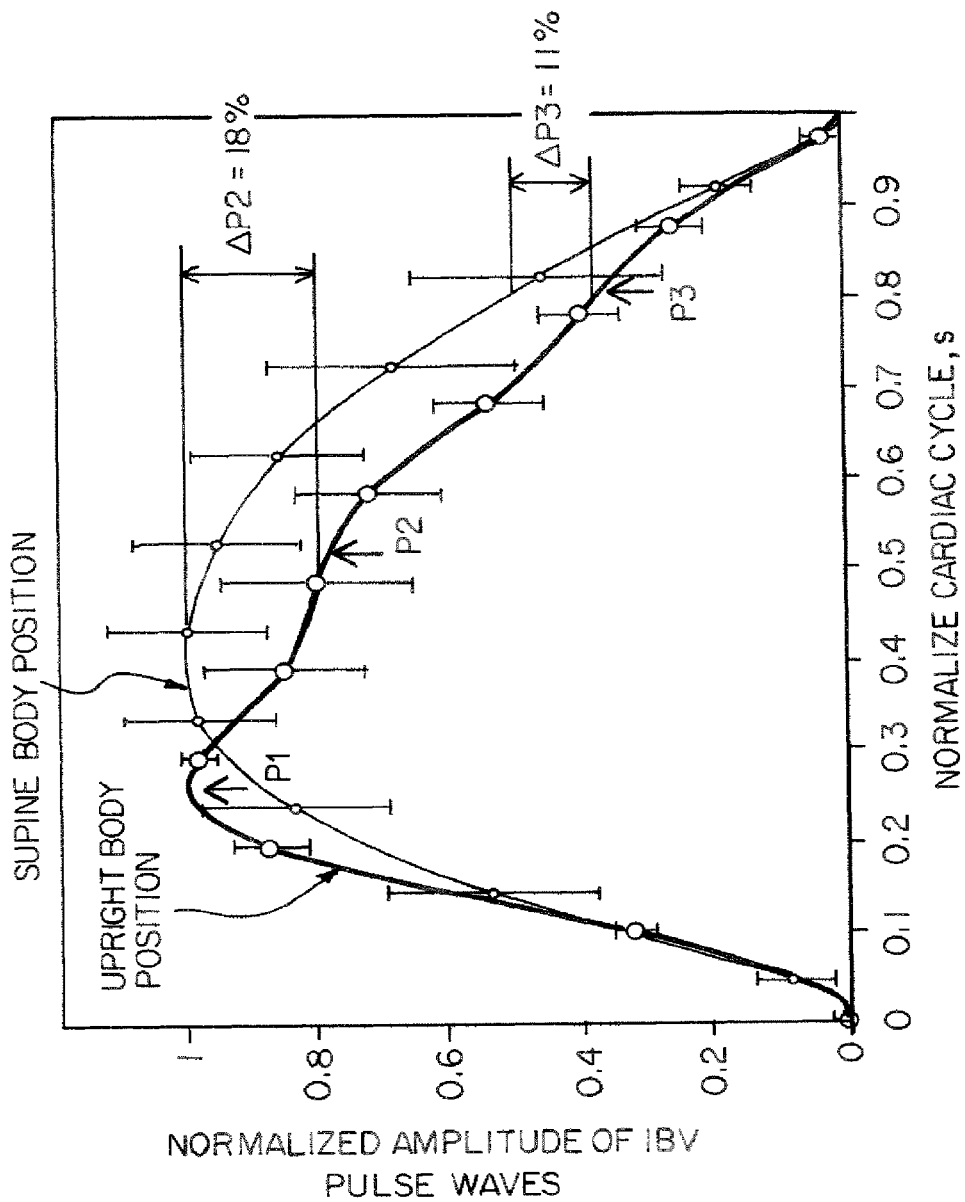
FIG. 19 illustrates IBV pulse wave averaged shapes of the group of 13 healthy volunteers in upright and supine body positions
Figure 19B:
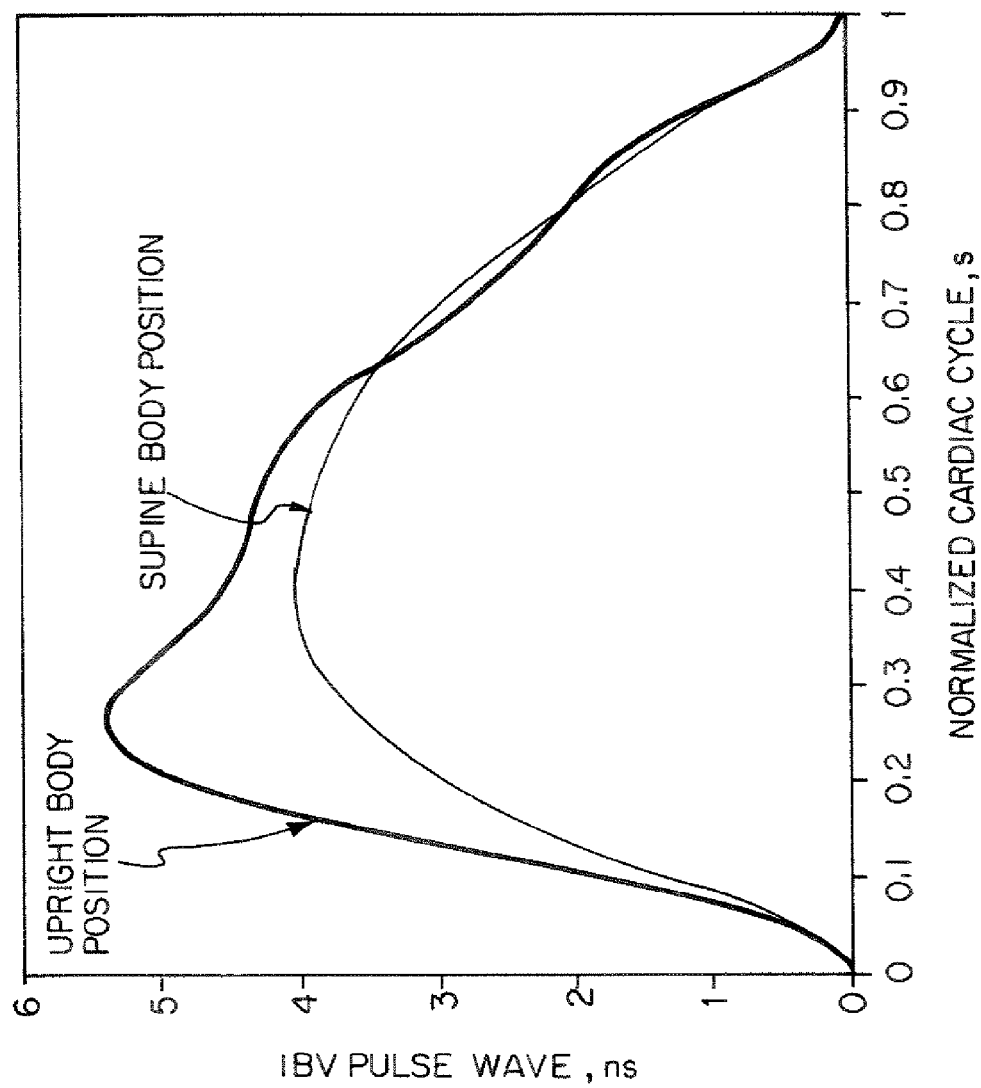
Figure 20:
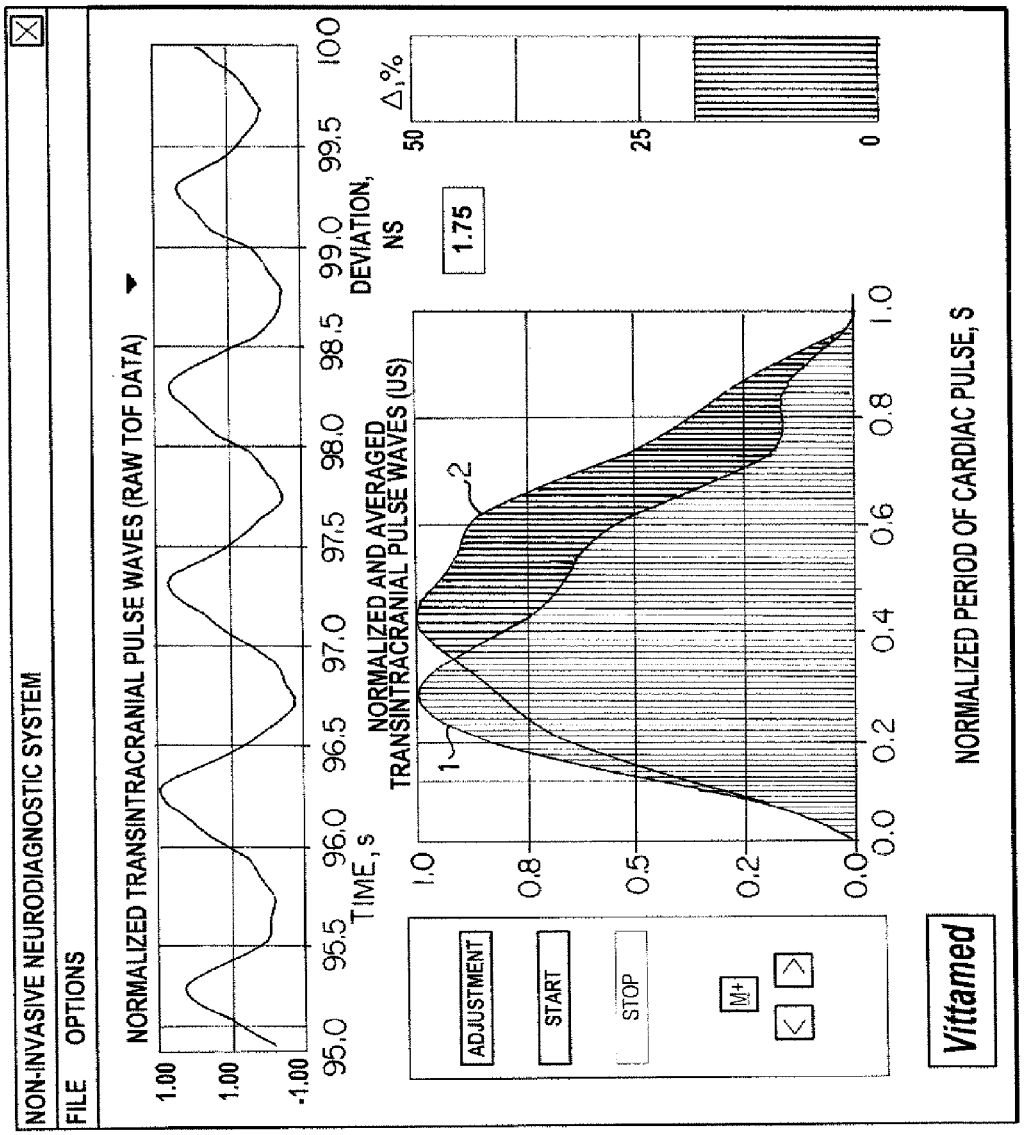
FIG. 20 illustrates the display panel of the non-invasive Vittamed monitor for intracranial blood volume pulse wave shape comparison.

FIG. 19 illustrates IBV pulse wave averaged shapes of a group of 13 healthy volunteers in upright and supine body positions: a) with marked P1, P2 and P3 subwaves and their differences $\Delta P2=18\%$ and $\Delta P3=11\%$ which were caused by body posture Vertical bars show physiological fluctuations of pulse wave shape expressed as +/−SD for all the group of healthy volunteers; b) non-normalized IBV pulse waves in upright and supine body postures FIG. 20 illustrates the display panel of the non-invasive Vittamed monitor for intracranial blood volume pulse wave shape comparison. Two IBV pulse waves are shown in normalised window with dimensions 1.0×1.0: reference wave (left wave) in upright body position the wave under comparison (right wave) in supine body posture when ICP has been elevated.

Figure 21:
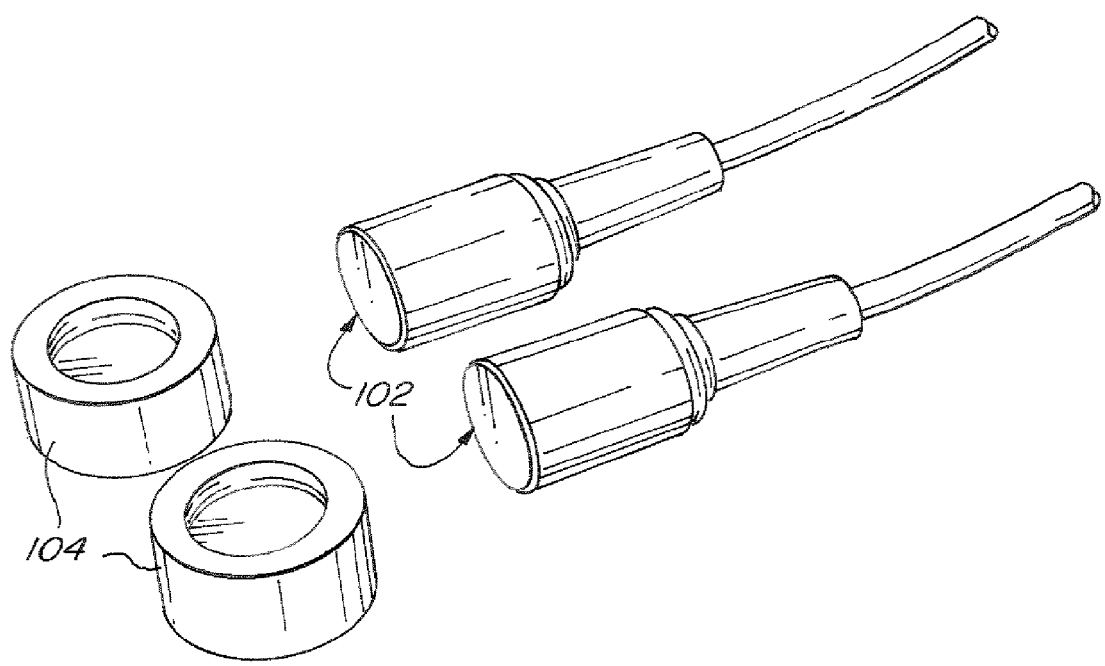
FIG. 21 illustrates two ultrasonic transducers and sonopads with supporting rings.

FIG. 21 illustrates two ultrasonic transducers 102 and sonopads with supporting rings. The gelpads 104 are made of supporting rings and sonopads, and the sonopads are made of a gel-like material and are positioned inside the supporting ring.

Figure 22:
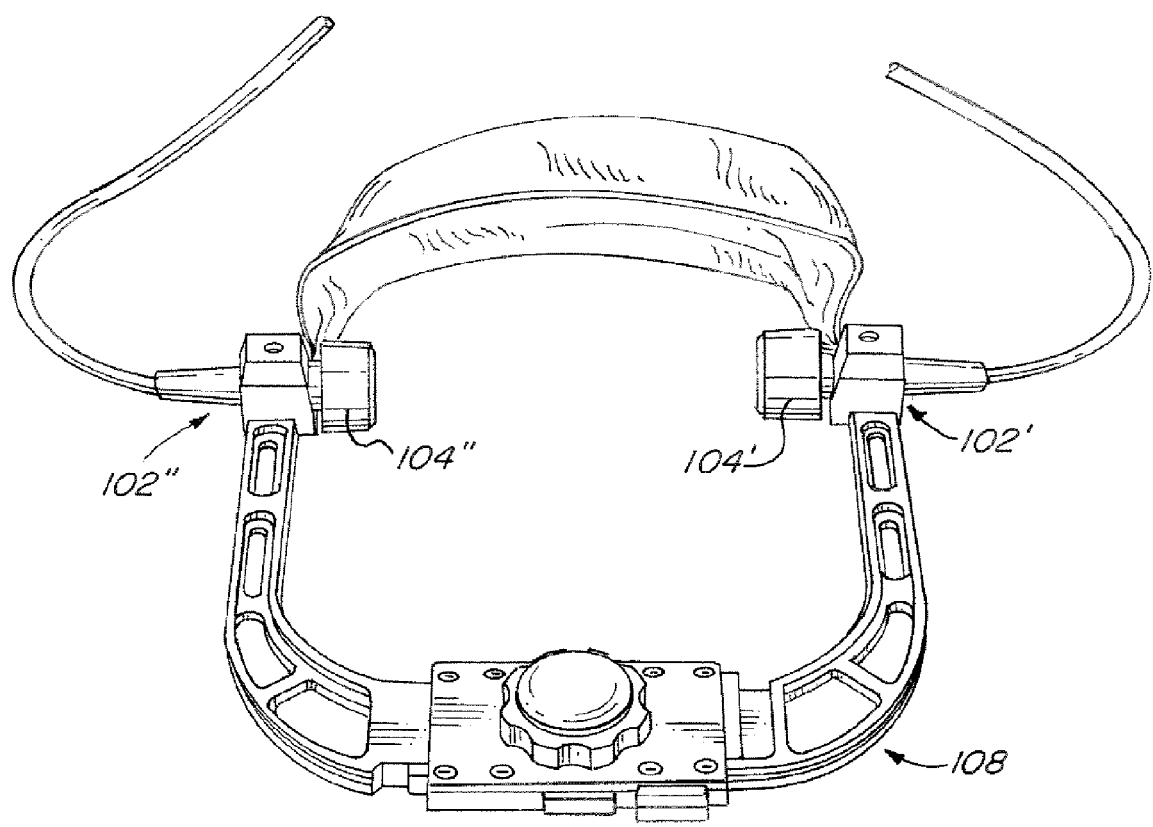
FIG. 22 illustrates a mechanical frame with ultrasonic transducers, sonopads and supporting rings.

FIG. 22 illustrates an embodiment of the mechanical frame 108 with ultrasonic transducers 102',102", sonopads and supporting rings.

Figure 23:
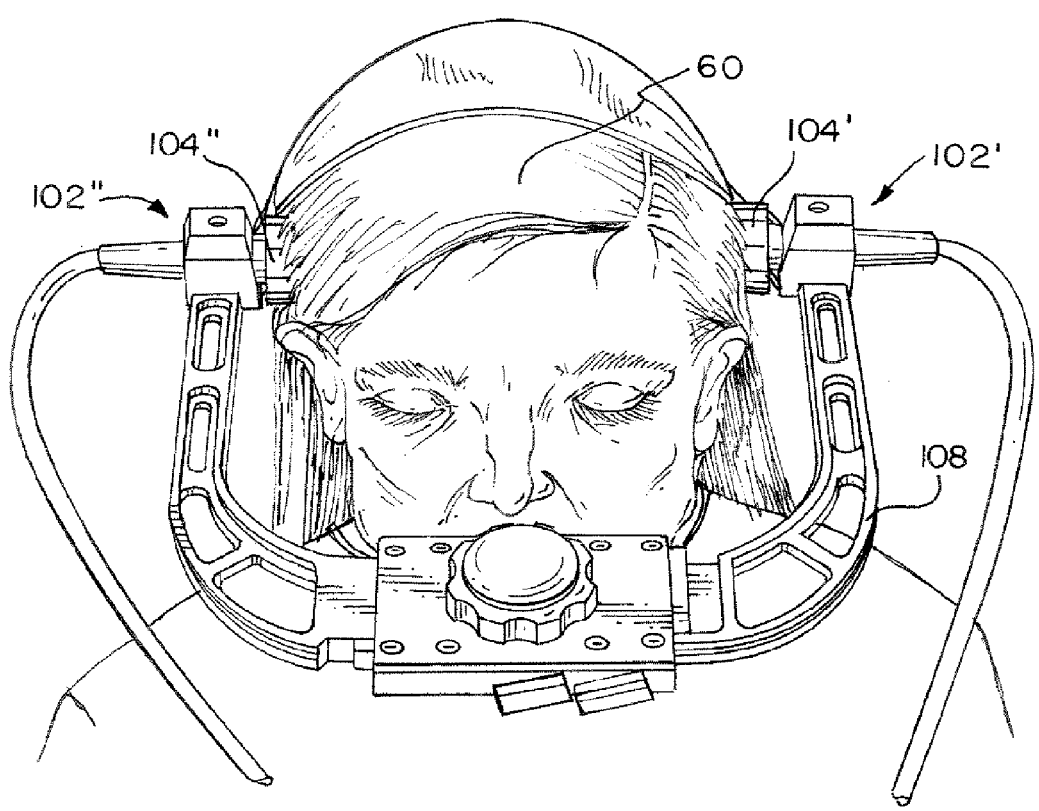
FIG. 23 illustrates typical position of mechanical frame fixation on the human head.

FIG. 23 illustrates one possible position of an embodiment of the mechanical frame 108 on the human head 60.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A device for measuring intracranial contents' volume change of a patient's head comprising:
   a first gel pad and a second gel pad adapted to be positioned on either side of the patient's head respectively; and
   a first ultrasonic transducer and a second ultrasonic transducer positioned adjacent to said first and second gel pads respectively;
   said first and second ultrasonic transducers each comprising:
   a piezoceramic disc; and
   a piezoceramic ring encircling said piezoceramic disc.

2. The device according to claim 1 further comprising:
   a first two-dimensional scanner positioned adjacent to said first ultrasonic transducer; and
   a second two-dimensional scanner positioned adjacent to said second ultrasonic transducer.

3. The device according to claim 2 further comprising a first polyvinylidene fluoride piezoelectric film ultrasonic transducer positioned between said first gel pad and said first ultrasonic transducer.

4. The device according to claim 3 further comprising a second polyvinylidene fluoride piezoelectric film ultrasonic transducer positioned between said second gel pad and said second ultrasonic transducer.

5. The device according to claim 4 wherein said first and second polyvinylidene fluoride piezoelectric film ultrasonic transducers are at least 10.0 MHz super wide band transducers.

6. The device according to claim 5 wherein said first and second ultrasonic transducers are 2.0 MHz wide band ceramic ultrasonic transducers.

7. The device according to claim 4 wherein a first and a second ultrasonic pulse are generated by the first and second ultrasonic transducers respectively, where the first and second ultrasonic pulses pass through the first and second polyvinylidene fluoride piezoelectric film ultrasonic transducer, where each of the first and second polyvinylidene fluoride piezoelectric film ultrasonic transducer are provided with outputs transmitting electrical pulses corresponding to the transmitted first and second ultrasonic pulses and transmitting electrical pulses corresponding to a first and a second ultrasonic echo pulse received by the first and second polyvinylidene fluoride piezoelectric film ultrasonic transducers respectively.

8. The device according to claim 7 further comprising a time division multiplexer coupled to and receiving the outputs from the first and second polyvinylidene fluoride piezoelectric film ultrasonic transducers.

9. The device according to claim 8 further comprising a computer coupled to said time division multiplexer.

10. The device according to claim 9 further comprising a reference clock coupled to said time division multiplexer.

11. The device according to claim 10 further comprising a timing generator coupled to said time division multiplexer.

12. The device according to claim 11 further comprising an analog-to-digital converter and a digital signal processor or complex programmable logic device or field programmable gate array coupled to said computer and said timing generator.

13. The device according to claim 9 further comprising a TT/D converter coupled to said computer and said time division multiplexer.

14. The device according to claim 9 further comprising a IP/D converter coupled to said computer and said time division multiplexer, said IP/D converter measuring the internal period of ultrasonic signals.

15. The device according to claim 1 wherein said first gel pad comprises a reflecting surface that is multi-planar such that reflected ultrasonic signals have substantially the same direction as transmitted ultrasonic signals.

16. The device according to claim 15 wherein said second gel pad comprises a reflecting surface that is multi-planar such that reflected ultrasonic signals have substantially the same direction as transmitted ultrasonic signals.

17. A device for measuring intracranial contents' volume change of a patient's head comprising:
   a first gel pad adapted to be positioned on a first side of the patient's head;
   a second gel pad adapted to be positioned on a second side of the patient's head;
   a first ultrasonic transducer positioned adjacent to said first gel pad, said first ultrasonic transducer including:
   a first piezoceramic disc; and
   a first piezoceramic ring encircling said first piezoceramic disc;
   a second ultrasonic transducer positioned adjacent to said second gel pad, said second ultrasonic transducer including:
   a second piezoceramic disc; and
   a second piezoceramic ring encircling said second piezoceramic disc;

a first scanner positioned adjacent to said first ultrasonic transducer;

a second scanner positioned adjacent to said second ultrasonic transducer;

a time division multiplexer coupled to said first and second ultrasonic transducers;

a computer coupled to said time division multiplexer; and a display coupled to said computer.

18. The device according to claim 17 further comprising:

a first polyvinylidene fluoride piezoelectric film ultrasonic transducer positioned between said first gel pad and said first ultrasonic transducer; and a second polyvinylidene fluoride piezoelectric film ultrasonic transducer positioned between said second gel pad and said second ultrasonic transducer.

19. The device according to claim 18 wherein a first and a second ultrasonic pulse are generated by the first and second ultrasonic transducers respectively, where the first and second ultrasonic pulses pass through the first and second polyvinylidene fluoride piezoelectric film ultrasonic transducer, where each of the first and second polyvinylidene fluoride piezoelectric film ultrasonic transducer are provided with outputs transmitting electrical pulses corresponding to the transmitted first and second ultrasonic pulses and transmitting electrical pulses corresponding to a first and a second ultrasonic echo pulse received by the first and second polyvinylidene fluoride piezoelectric film ultrasonic transducers respectively.

20. The device according to claim 17 wherein said first and second gel pads comprise reflecting surfaces that are multi-planar such that reflected ultrasonic signals have substantially the same direction as transmitted ultrasonic signals.

21. A method for measuring intracranial contents' volume change of a patient's head comprising the steps of:

positioning a first gel pad on a first side of the patient's head;

positioning a second gel pad on a second side of the patient's head;

positioning a first ultrasonic transducer adjacent to the first gel pad, the first ultrasonic transducer having a first piezoceramic disc and a first piezoceramic ring encircling the first piezoceramic disc;

positioning a second ultrasonic transducer adjacent to the second gel pad, the second ultrasonic transducer having a second piezoceramic disc and a second piezoceramic ring encircling the second piezoceramic disc;

generating first and second ultrasonic pulses with the first and second ultrasonic transducers respectively;

transmitting the first ultrasonic pulse through the patient's head at a first signal transmission direction;

transmitting the second ultrasonic pulse through the patient's head at a second signal transmission direction;

receiving a first ultrasonic echo pulse with the first ultrasonic transducer at a first echo signal receiving direction; and receiving a second ultrasonic echo pulse with the second ultrasonic transducer at a second echo signal receiving direction.

22. The method according to claim 21 further comprising the step of:

receiving a first ultrasonic transintracranial pulse with the first ultrasonic transducer at a first transintracranial signal receiving direction; and receiving a second ultrasonic transintracranial pulse with the second ultrasonic transducer at a second transintracranial signal receiving direction.

23. The method according to claim 22 further comprising the steps of:

positioning a first scanner adjacent to the first ultrasonic transducer; and positioning a second scanner adjacent to the second ultrasonic transducer.

24. The method according to claim 23 further comprising the steps of:

scanning the first signal transmission direction and first echo signal receiving direction with the first ultrasonic scanner to identify the optimal first signal transmission direction and optimal first echo signal receiving direction;

scanning the second signal transmission direction and second echo signal receiving direction with the second ultrasonic scanner to identify the optimal second signal transmission direction and optimal second echo signal receiving direction;

scanning the first signal transmission direction and first transintracranial signal receiving direction with the first ultrasonic scanner to identify the optimal first transintracranial signal receiving direction; and scanning the second signal transmission direction and second transintracranial signal receiving direction with the second ultrasonic scanner to identify the optimal second transintracranial signal receiving direction.

25. The method according to claim 24 further comprising the steps of positioning a first polyvinylidene fluoride piezoelectric film ultrasonic transducer between the first gel pad and the first ultrasonic transducer and positioning a second polyvinylidene fluoride piezoelectric film ultrasonic transducer between the second gel pad and the second ultrasonic transducer.

26. The method according to claim 25 wherein the first and second ultrasonic pulses generated by the first and second ultrasonic transducers pass through first and second polyvinylidene fluoride piezoelectric film ultrasonic transducers, where each of the first and second polyvinylidene fluoride piezoelectric film ultrasonic transducers are provided with outputs transmitting electrical pulses corresponding to the transmitted first and second ultrasonic pulses and transmitting electrical pulses corresponding to ultrasonic echo pulses received by the first and second polyvinylidene fluoride piezoelectric film ultrasonic transducers.

27. The method according to claim 26 further comprising the steps of coupling the outputs first and second polyvinylidene fluoride piezoelectric film ultrasonic transducers to a time division multiplexer.

28. The method according to claim 27 further comprising the steps of transmitting information from the time division multiplexer to a computer and displaying the information on a display.

29. The method according to claim 21 further comprising the steps of forming a reflecting surface of the first gel pad as a multi-planar surface such that reflected ultrasonic signals have substantially the same direction as transmitted ultrasonic signals.

30. The method according to claim 29 further comprising the steps of forming a reflecting surface of the second gel pad as a multi-planar surface such that reflected ultrasonic signals have substantially the same direction as transmitted ultrasonic signals.

31. A method for measuring intracranial contents' volume change of a patient's head comprising the steps of:

positioning a first ultrasonic transducer on a first side of the patient's head;

positioning a second ultrasonic transducer on a second side of the patient's head, on a substantially opposite side of the patient's head from the first ultrasonic transducer;

said first and second ultrasonic transducers each comprising:
- a piezoceramic disc; and
- a piezoceramic ring encircling said piezoceramic disc;

positioning a first scanner adjacent to the first ultrasonic transducer;

positioning a second scanner adjacent to the second ultrasonic transducer;

generating a first ultrasonic pulse with the first ultrasonic transducer;

transmitting the first ultrasonic pulse through a patient's head at a first signal transmission direction;

generating a second ultrasonic pulse with the second ultrasonic transducer;

transmitting the second ultrasonic pulse through a patient's head at a second signal transmission direction;

generating a first electrical pulse corresponding to the transmitted first ultrasonic pulse;

measuring a first echo pulse at a first echo signal receiving direction corresponding to an echo signal of the transmitted first ultrasonic pulse;

generating a first echo electrical pulse corresponding to the measured first echo pulse;

generating a second electrical pulse corresponding to the transmitted second ultrasonic pulse;

measuring a second echo pulse at a second echo signal receiving direction corresponding to an echo signal of the transmitted second ultrasonic pulse;

generating a second echo electrical pulse corresponding to the measured second echo pulse;

scanning the first signal transmission direction and first echo signal receiving direction with the first ultrasonic scanner to identify the optimal first signal transmission direction and optimal first echo signal receiving direction; and scanning the second signal transmission direction and second echo signal receiving direction with the second ultrasonic scanner to identify the optimal second signal transmission direction and optimal second echo signal receiving direction.

32. The method according to claim 31 further comprising the steps of inputting the first and second electrical pulses into a multiplexer.

33. The method according to claim 32 further comprising the steps of inputting the first and second echo electrical pulses into the multiplexer.

* * * * *